US007785862B2

(12) United States Patent
Kim et al.

(10) Patent No.: US 7,785,862 B2
(45) Date of Patent: Aug. 31, 2010

(54) THIN FILM COATED MICROWELL ARRAYS

(75) Inventors: Jong-Bum Kim, Branford, CT (US);
Steven Martin Lefkowitz, Branford, CT (US); John Nobile, Fairfield, CT (US)

(73) Assignee: 454 Life Sciences Corporation, Branford, CT (US)

( * ) Notice: Subject to any disclaimer, the term of this patent is extended or adjusted under 35 U.S.C. 154(b) by 324 days.

(21) Appl. No.: 11/102,075

(22) Filed: Apr. 7, 2005

(65) Prior Publication Data
US 2006/0228716 A1 Oct. 12, 2006

(51) Int. Cl.
*C12M 1/36* (2006.01)
*G01N 15/06* (2006.01)
(52) U.S. Cl. ............ 435/283.1; 435/287.2; 435/288.4; 422/68.1; 422/82.05
(58) Field of Classification Search .................. None
See application file for complete search history.

(56) References Cited
U.S. PATENT DOCUMENTS

| 5,632,957 | A | 5/1997 | Heller et al. |
| 6,377,721 | B1 | 4/2002 | Walt et al. |
| 6,395,483 | B1 | 5/2002 | Patil et al. |
| 6,440,645 | B1 | 8/2002 | Yon-Hin et al. |
| 6,448,089 | B1 | 9/2002 | Vuong ................. 436/164 |
| 6,495,104 | B1 * | 12/2002 | Unno et al. ............ 422/68.1 |
| 7,364,896 | B2 * | 4/2008 | Schembri ............. 435/287.1 |
| 2003/0068629 | A1 | 4/2003 | Rothberg et al. ........... 435/6 |
| 2003/0092171 | A1 | 5/2003 | Henck ................. 435/287.2 |
| 2004/0191924 | A1 | 9/2004 | Hunter et al. ............ 436/180 |
| 2004/0248161 | A1 | 12/2004 | Rothberg et al. ........... 435/6 |
| 2005/0244305 | A1 * | 11/2005 | Fujita ................. 422/102 |

FOREIGN PATENT DOCUMENTS

| WO | WO 99/28504 | 6/1999 |
| WO | WO 99/30823 | 6/1999 |
| WO | WO 01/18524 A2 | 3/2001 |
| WO | WO 01/20039 A2 | 3/2001 |
| WO | WO 02/077287 A1 | 10/2002 |
| WO | WO 02/078834 A2 | 10/2002 |
| WO | WO 2004/011912 A1 | 2/2004 |

OTHER PUBLICATIONS

Invitation to Pay Additional Fees for PCT/US2006/013494, mailed Aug. 17, 2006.
Leamon et al. *Electrophoresis*, 24:3769-3777 (2003).
Karabacak et al., "Enhances step coverage by oblique angle physical vapor deposition", *J. Appl. Physics*, 97:124504-1-124504-5 (2005).
Guenther, et al.; (1988) *Ron Willey, Opto Mechanik, Inc.*, "Reactive Ion Plating—A Novel Deposition Technique for Improved Optical Coatings", pp. 186-191.
Schmidt, et al.; (2000); *The Sol-Gel Gateway : Tutorial on Wet Coating Technologies*; "Wet Coating Technologies for Glass", pp. 1-19.

* cited by examiner

*Primary Examiner*—B J Forman
(74) *Attorney, Agent, or Firm*—Ivor R. Elrifi; Jennifer L. Loebach; Mintz, Levin, Cohn, Ferris, Glovsky and Popeo, P.C.

(57) ABSTRACT

The invention relates to a thin film coated array and the process of fabricating and using the array including methods of etching, depositing a thin film coating, preparing and using the thin film coated array.

16 Claims, 21 Drawing Sheets

Cross-Section SEMs of Coated FoFs

Figure 1
SEMs of Coated FoFs
Sputtered 5k mag.
A 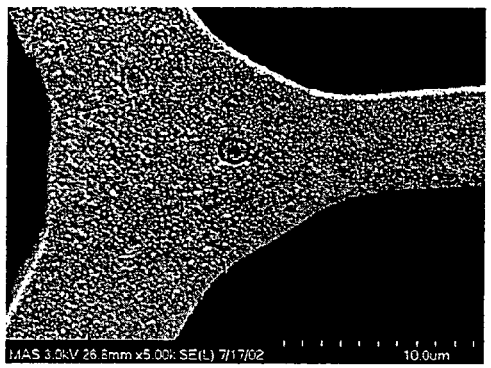
Sputtered 10k mag.
B 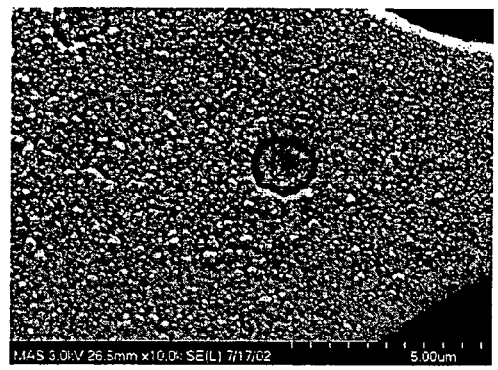
PECVD 5k mag.
C 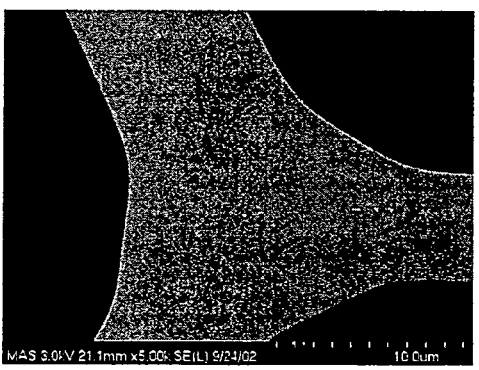
PECVD 10k mag.
D 
Ion-Plated 5k
E 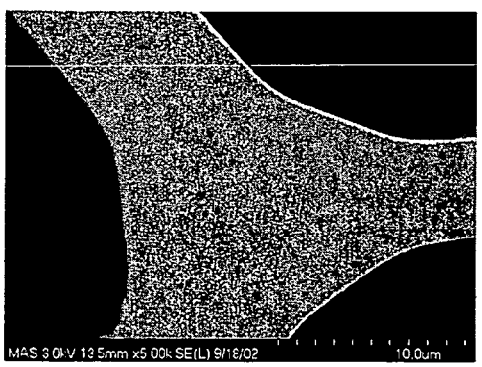
Ion-Plated 10k mag.
F 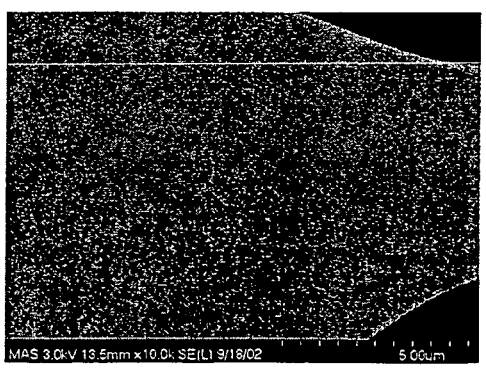

Figure 2
Cross-Section SEMs of Coated FOFs
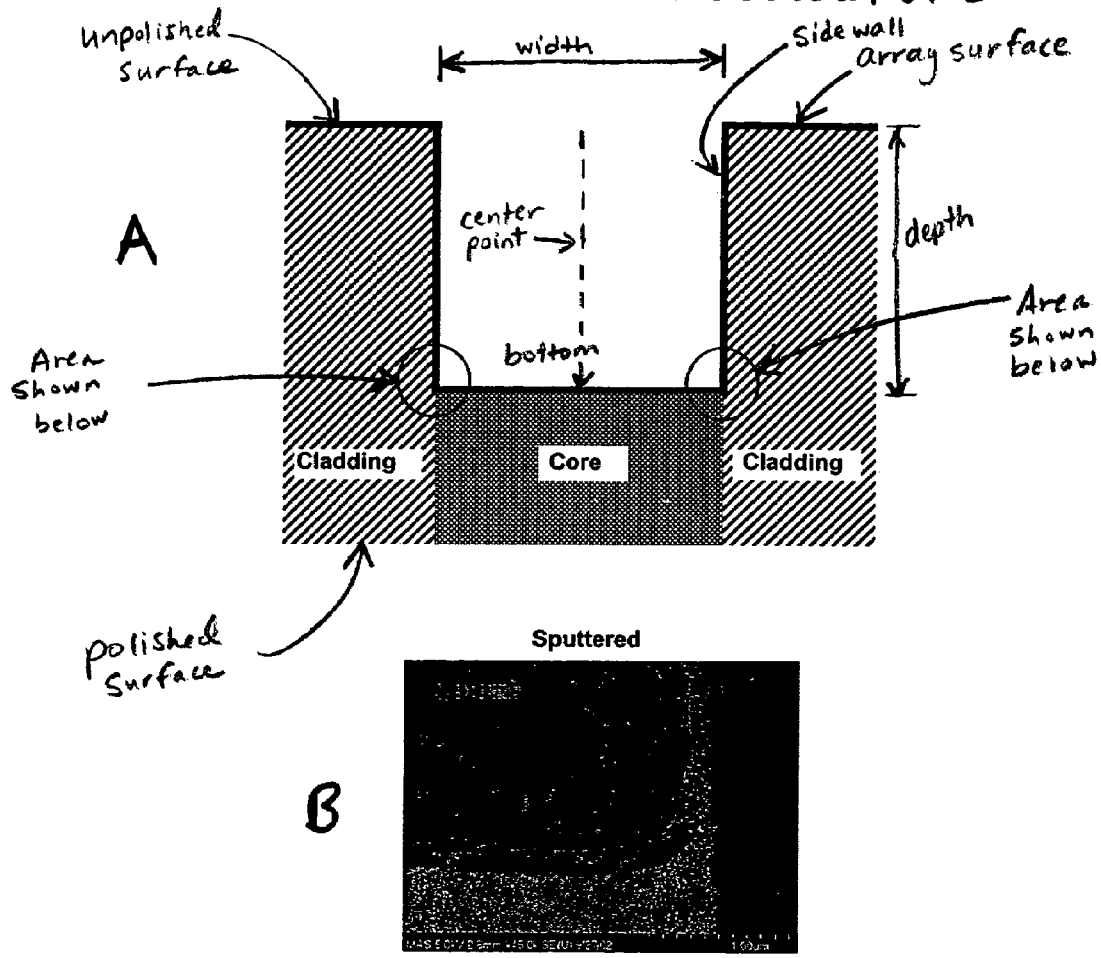
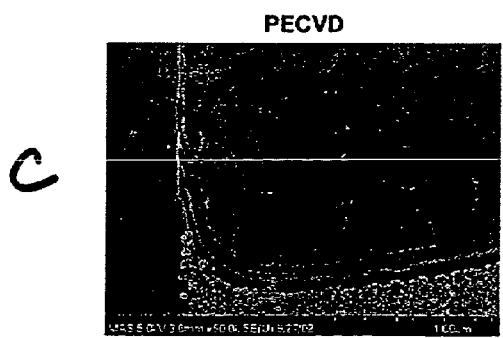
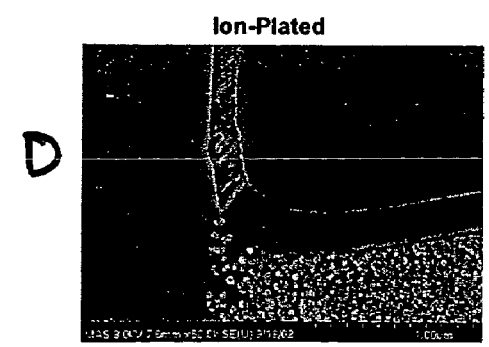

Schematic Diagram
Of Ion-Plating Process

PCR-Induced Sequencing Background Of Coated and Uncoated FoFs
(error bars = 95% CL for 3 samples)

Sequencing Performance Metrics of Coated and Uncoated FoFS

Figure 6
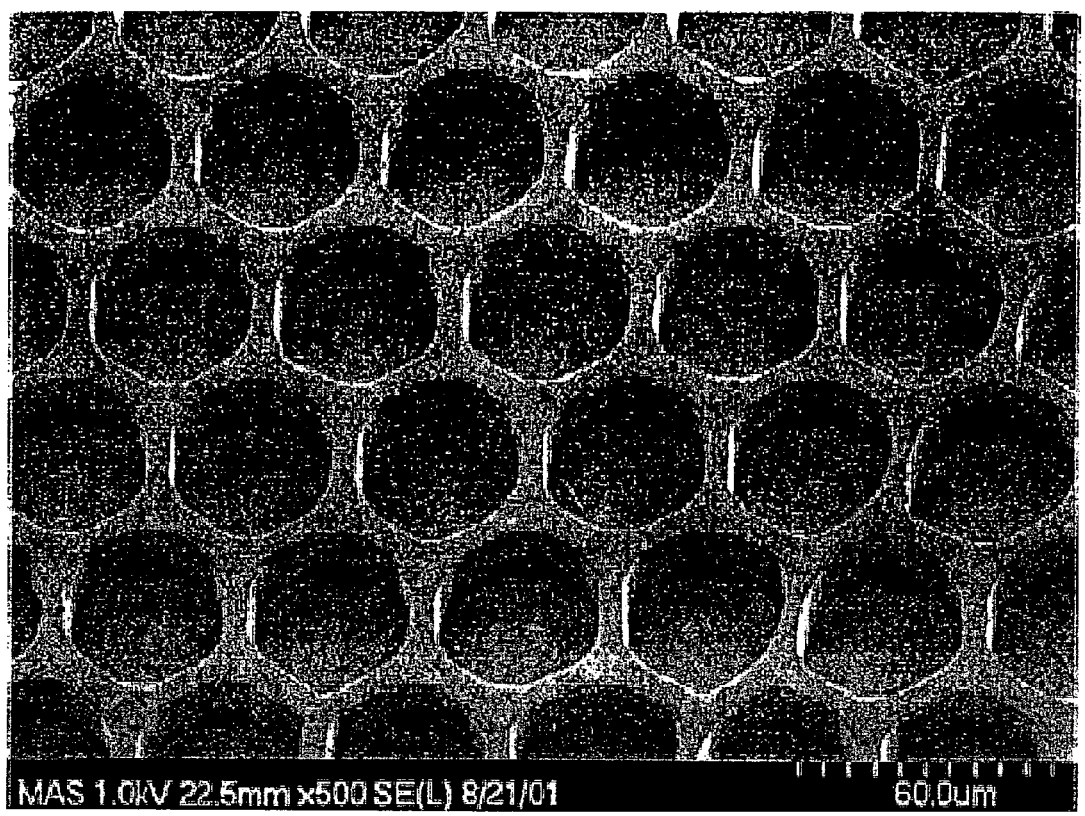
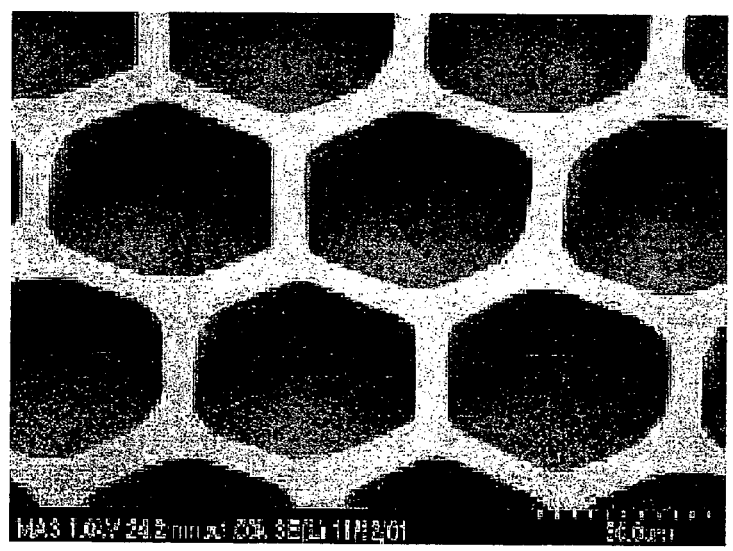

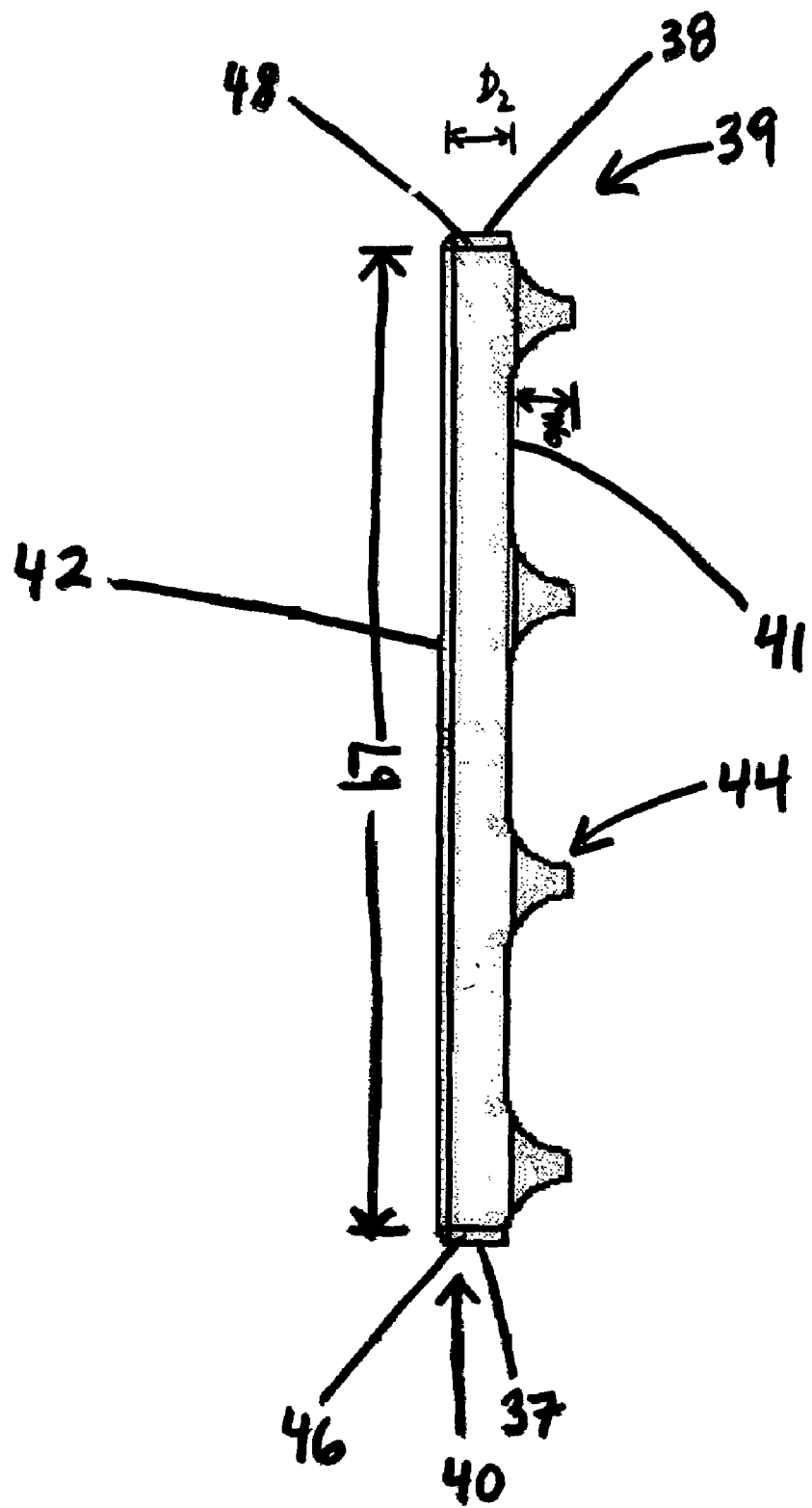

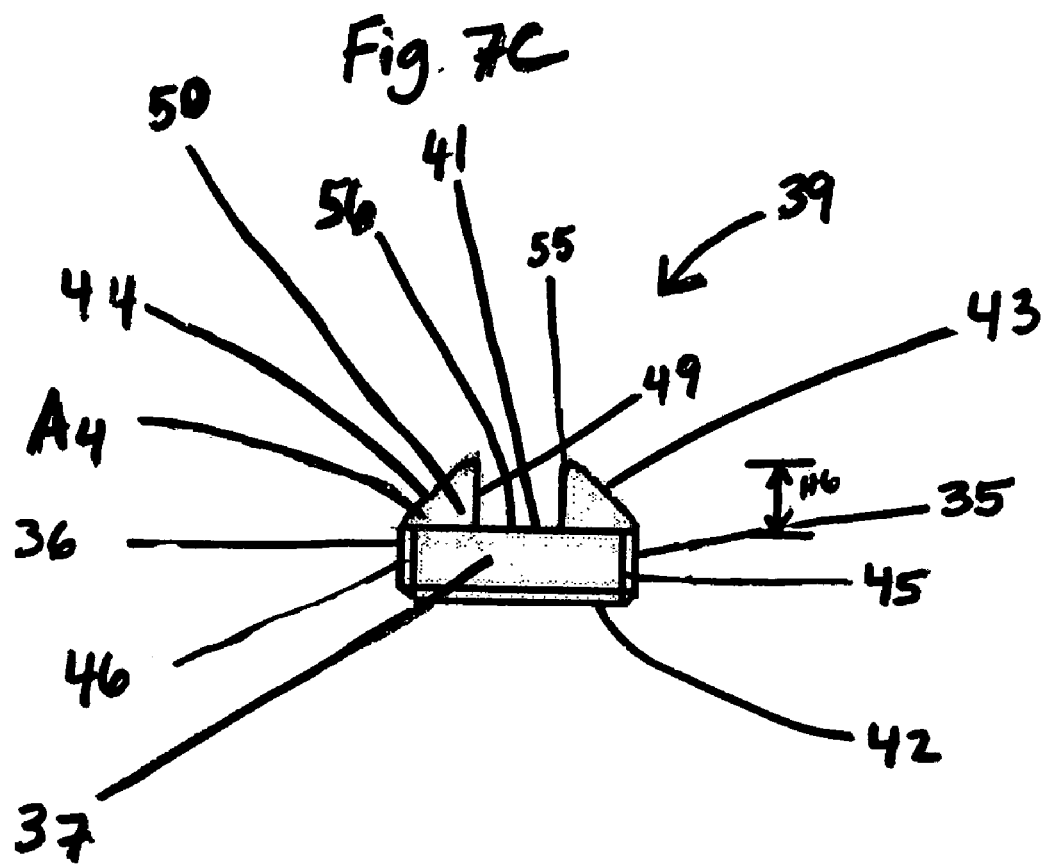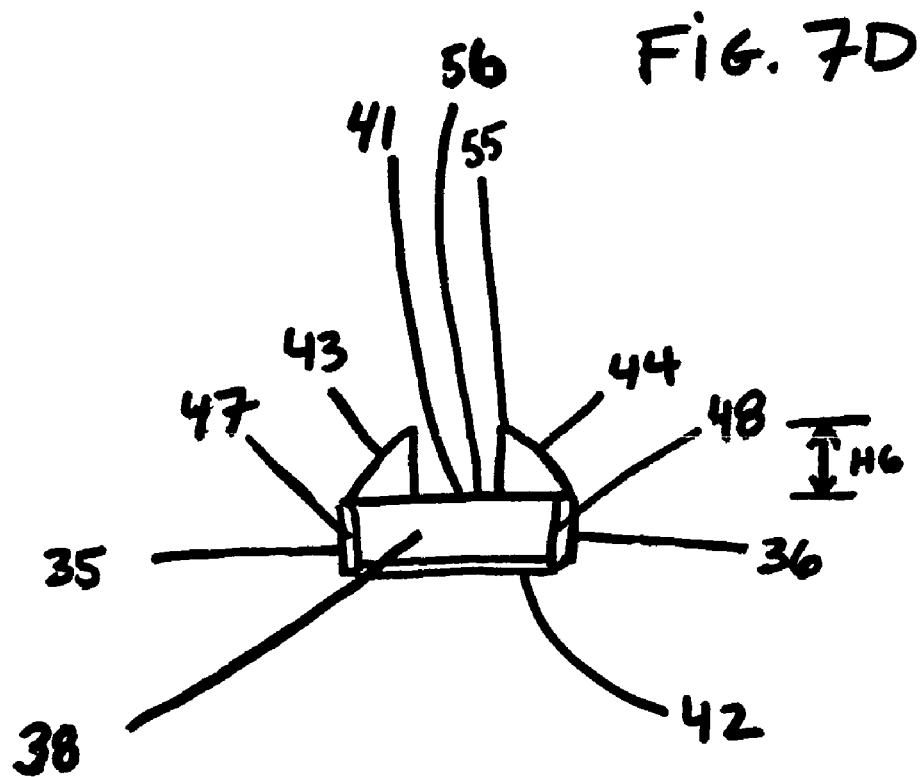

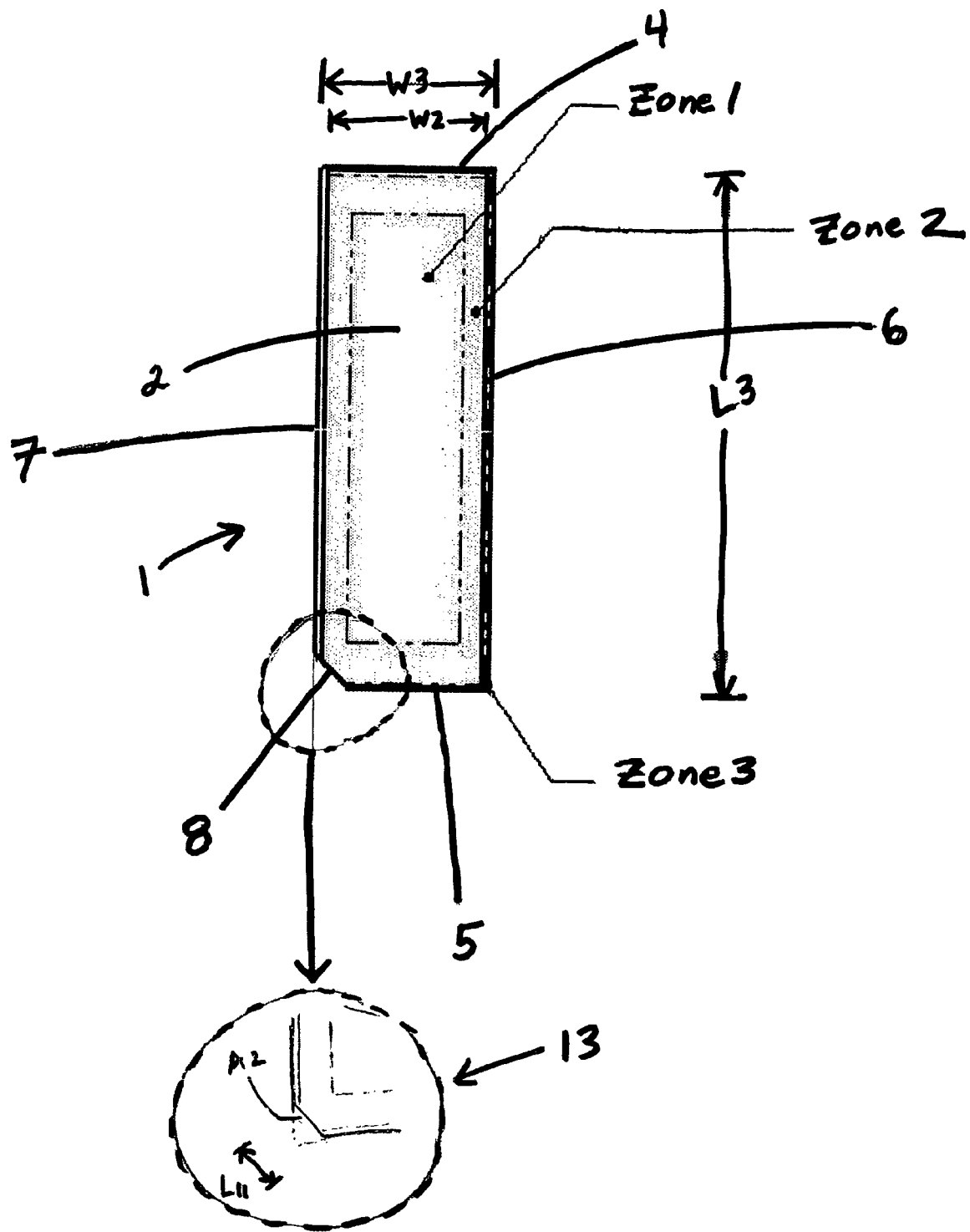

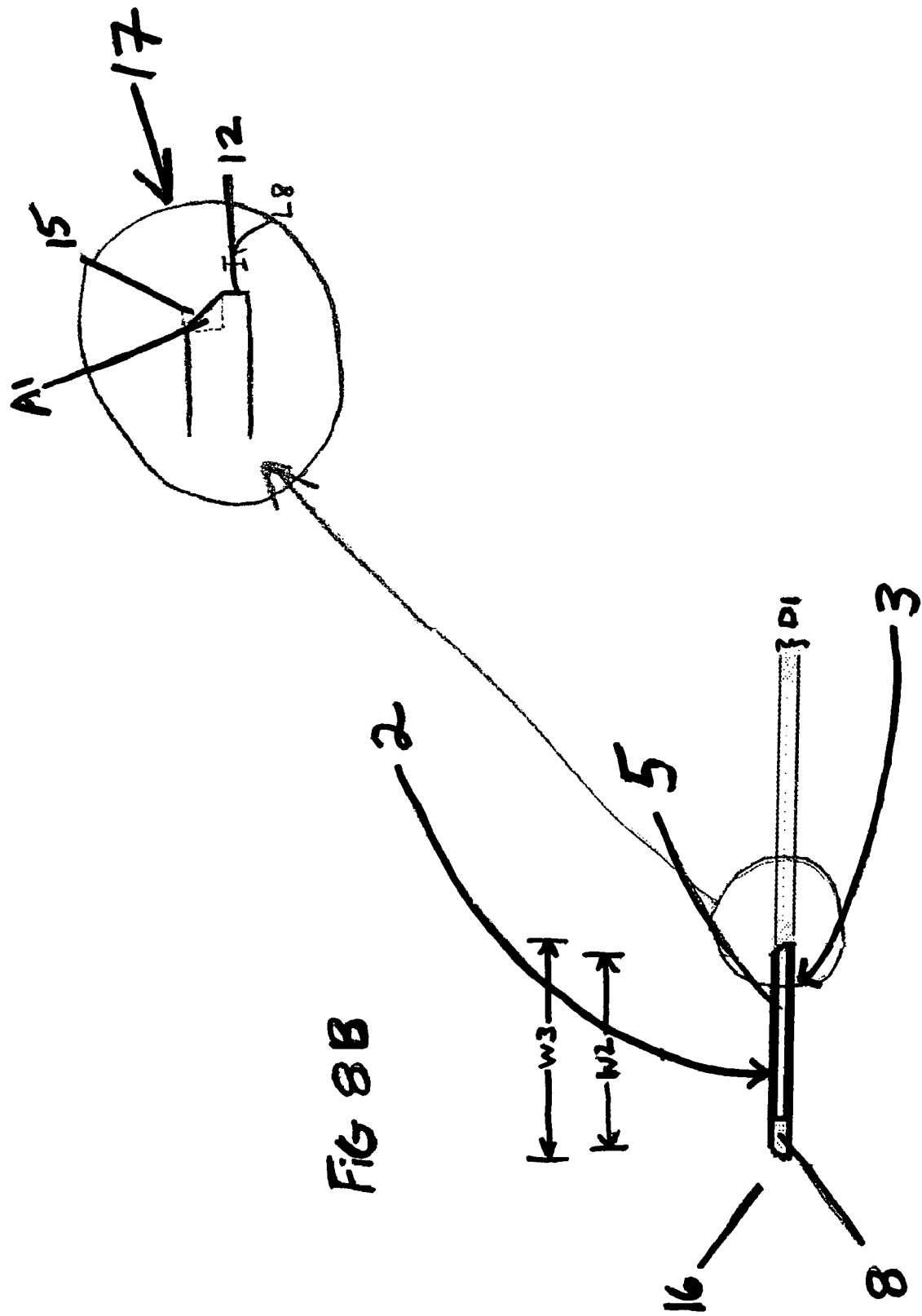

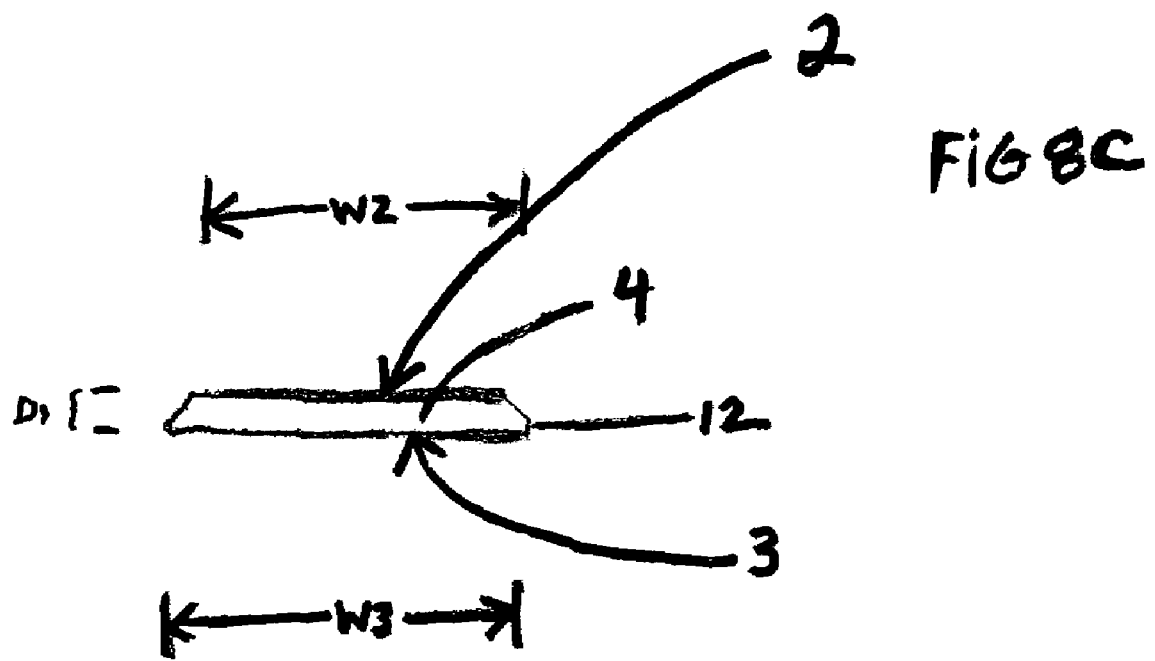

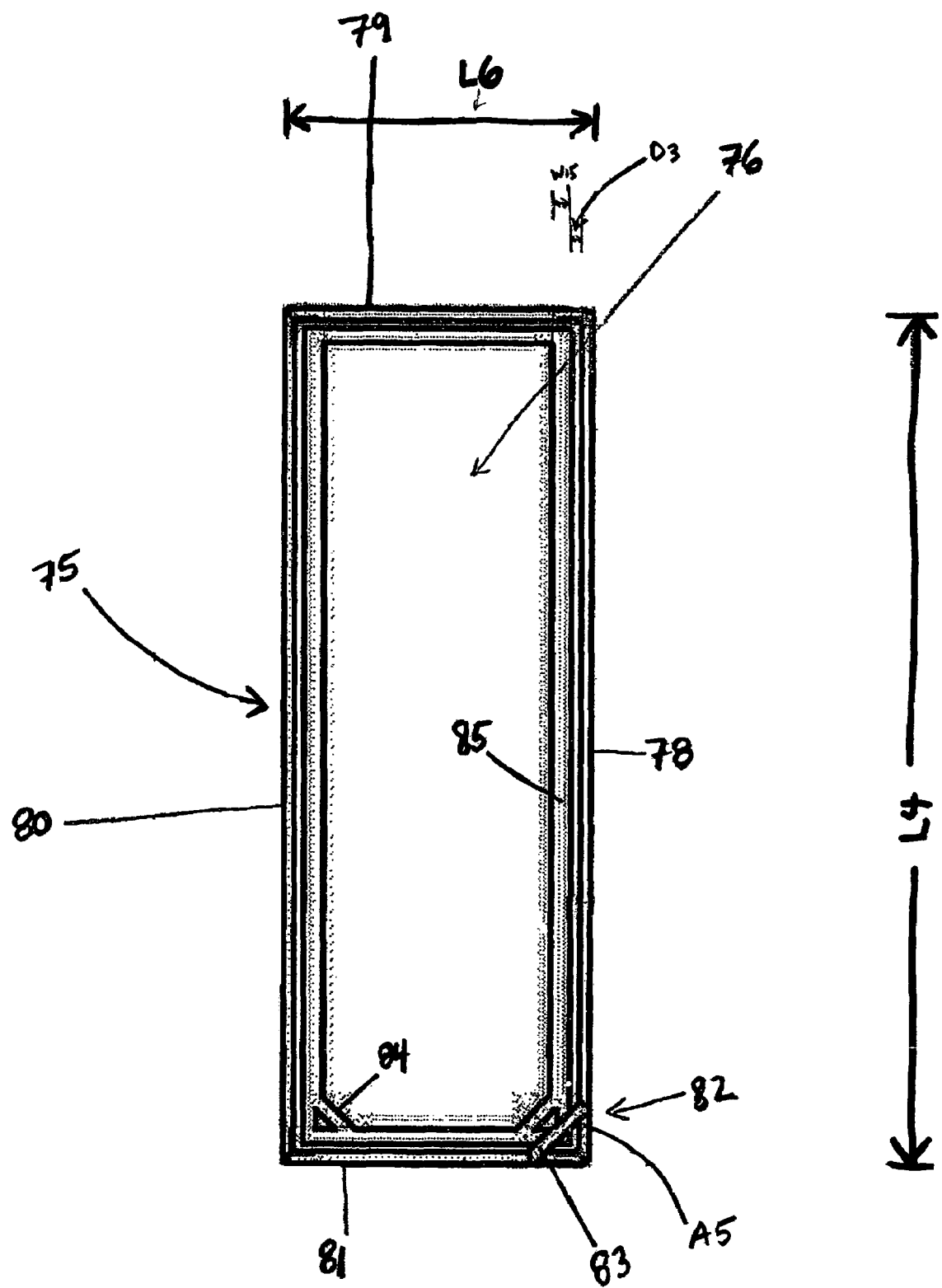

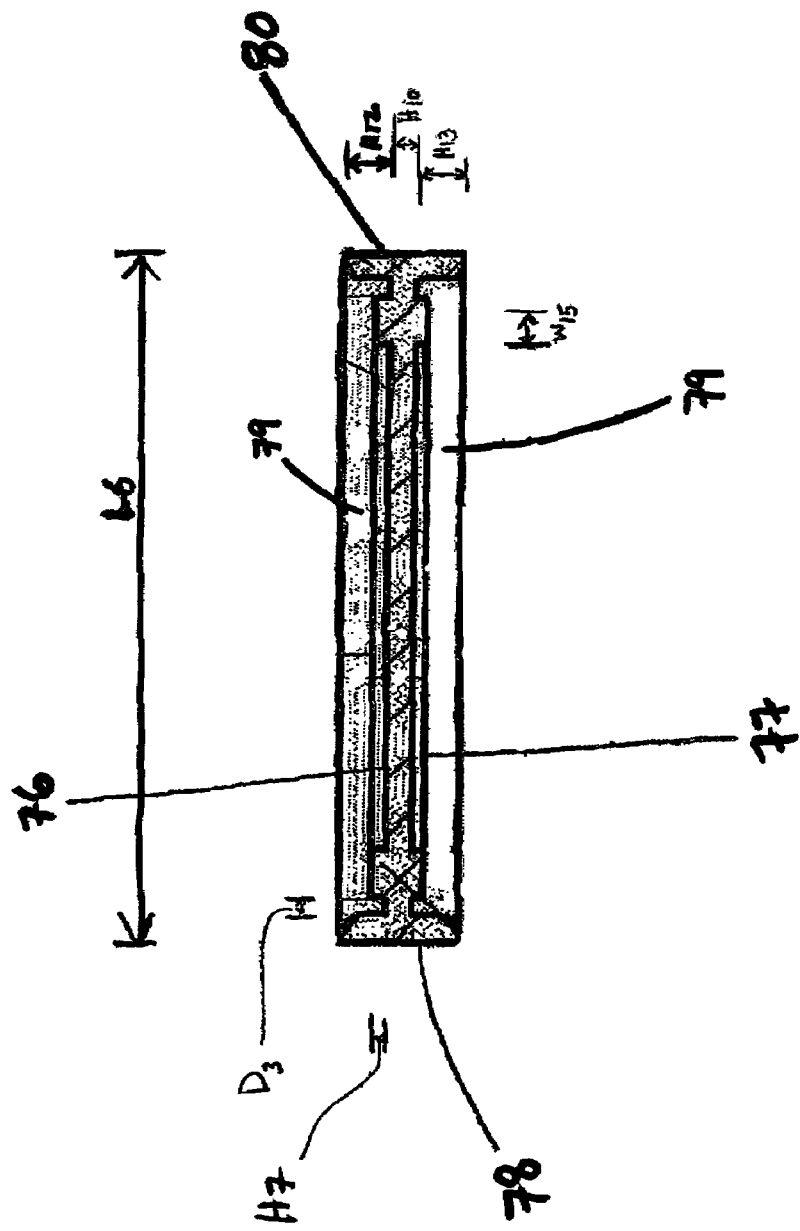

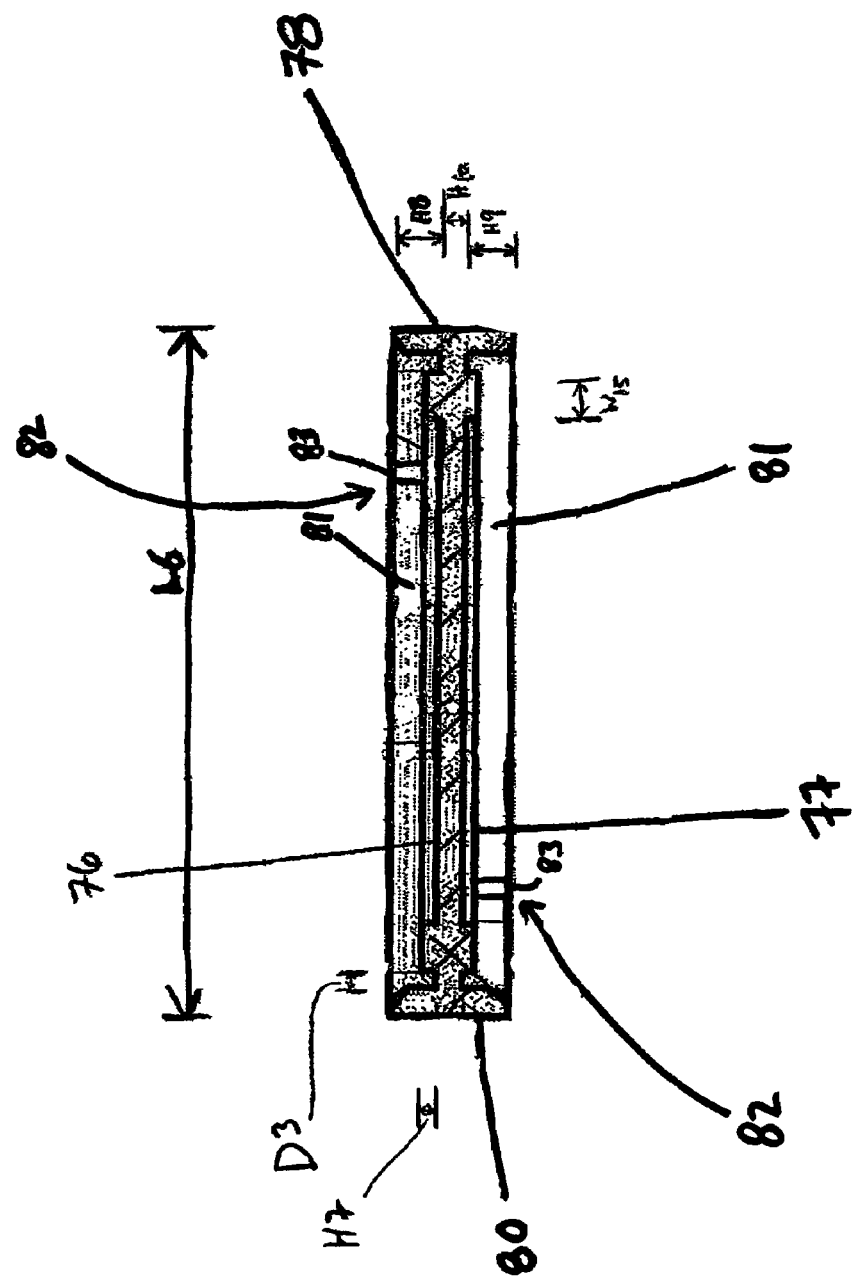

THIN FILM COATED MICROWELL ARRAYS

FIELD OF THE INVENTION

This invention relates to array compositions comprised of a substrate coated with a thin film. The invention includes the process of fabricating the array including methods of etching, depositing a thin film coating, preparing and using the thin film coated microwell array.

BACKGROUND OF THE INVENTION

The ability to perform parallel microanalysis on minute quantities of sample is important to the advancement of chemistry, biology, drug discovery and medicine. Today, the traditional 1536-well microtiter plate has been surpassed by microwell arrays which have an even greater number of reaction chambers and use lesser amounts of reagents due to efforts focused on maximizing time and cost efficiencies. Although there are several types of microwell arrays available, many microwell materials prove to be incompatible with the components of bioassays and chemical reactions and result in problems such as low sensitivity, high background signal, and lack of reproducibility. Thus, there continues to be a need for the development of improved microwell arrays.

One solution to the problem of incompatible materials is to apply a thin film coating of a compatible material to the microwell array to enhance its surface properties and function. Patil, et al. U.S. Pat. No. 6,395,483 has disclosed a method to coat polymeric substrates with mask layers comprised of metallic and metal-oxide for use in high-density microarray applications. Yon-Hin, et al. U.S. Pat. No. 6,440,645 has described a process to use a photoimageable thin film on a polymer substrate to form microwells or channels. Heller, et al. U.S. Pat. No. 5,632,957 describes the deposition of metal, insulator and passivation coatings of substrates to form microelectrode arrays, and to form wells over the individual microelectrodes. Walt, et al. U.S. Pat. No. 6,377,721 discloses the coating of microwell interior surfaces on fiber optic arrays with a thin film of a biologically compatible material, citing biopolymers, synthetic polymers, and metals as examples.

Certain fiber optic bundles have been used to create arrays. Several methods are known in the art for attaching functional groups (and detecting the attached functional groups) to reaction chambers etched in the ends of fiber optic bundles. See, e.g., Michael, et al., *Anal. Chem.* 70: 1242-1248 (1998); Ferguson, et al., *Nature Biotechnology* 14: 1681-1684 (1996); Healey and Walt, *Anal. Chem.* 69: 2213-2216 (1997). A pattern of reactive functional groups can also be created in the reaction chamber, using photolithographic techniques similar to those used in the generation of a pattern of reaction pads on a planar support. See, Healey, et al., *Science* 269: 1078-1080 (1995); Munkholm and Walt, *Anal. Chem.* 58: 1427-1430 (1986), and Bronk, et al., *Anal. Chem.* 67: 2750-2757 (1995).

An array of functional groups on a substrate can be constructed using lithographic techniques commonly used in the construction of electronic integrated circuits as described in, e.g., techniques for attachment described in U.S. Pat. Nos. 5,143,854, 5,445,934, 5,744,305, and 5,800,992; Chee et al., *Science* 274: 610-614 (1996); Fodor et al., *Nature* 364: 555-556 (1993); Fodor et al., *Science* 251: 767-773 (1991); Gushin, et al., *Anal. Biochem.* 250: 203-211 (1997); Kinosita et al., *Cell* 93: 21-24 (1998); Kato-Yamada et al., *J. Biol. Chem.* 273: 19375-19377 (1998); and Yasuda et al., *Cell* 93: 1117-1124 (1998). Photolithography and electron beam lithography sensitize the substrate with a functional group that allows attachment of a reactant (e.g., proteins or nucleic acids). See e.g., Service, *Science* 283: 27-28 (1999); Rai-Choudhury, HANDBOOK OF MICROLITHOGRAPHY, MICROMACHNING, AND MICROFABRICATION, VOLUME I: MICROLITHOGRAPHY, Volume PM39, SPIE Press (1997). Alternatively, an array of functional groups can be generated using thin film technology as described in Zasadzinski et al., *Science* 263: 1726-1733 (1994).

One major disadvantage of this type of fiber optic array is the constraint of the materials comprising the fiber optic bundle. To act as an efficient waveguide, each fiber element must consist of a high refractive index core surrounded by a low refractive index cladding. These fiber optic materials are often incompatible with many reaction conditions, particularly assays which are often conducted in aqueous solutions and contain sensitive enzymatic reagents. Two major sources of incompatibility are the dissolution of the fiber optic substrate into the solution contained in the reaction chamber and the actual chemical reaction of the fiber optic substrate with components contained in the chamber. For example, core components, such as barium and lanthanum oxides, can form hydroxides which are water soluble, particularly at elevated temperatures. Multivalent heavy metals, such as barium and lanthanum, can interact unfavorably with enzymes, especially those enzymes with metal ion co-factors. Heavy metal oxide surfaces tend to be positively charged at the solution interface, and tend to non-specifically bind negatively charged species such as nucleic acids. All of these effects will tend to degrade the performance of assays and reactions conducted in the fiber optic reaction chambers. Increasing miniaturization also tends to exacerbate these unfavorable effects.

The fact that the fiber optic substrate must be comprised of two materials (core and cladding) also can limit the effectiveness of any surface modification of the reaction chambers with a monolayer (e.g. functional groups). For example, a singly charged surface can be modified by binding to the charged surface of functionalized polyelectrolytes which contain an opposite charge. The core and cladding materials of the fiber optic substrate each have different types of charges. Thus, any modification of the fiber optic substrate with a single polyelectrolyte is impossible since the substrate does not contain a single uniform charge.

One way to alleviate these problems is to coat the array substrate with a thin film using methods described herein. In general, the discussion herein is focused on fiber optic substrates, although other substrates as described below may be used in any embodiment described herein.

Due to technical difficulties in currently used processes for coating arrays, the range of assays that can be conducted in microwell arrays remains less than would be desired. Accordingly, there is a clear need for microwell arrays which are compatible for any assay or reaction conditions.

BRIEF SUMMARY OF THE INVENTION

This invention relates to array compositions comprised of a substrate coated with a thin film. In one embodiment, the array comprises a substrate, wherein the substrate is a fiber optic faceplate which has a surface comprising a plurality of reaction chambers and a thin film coating. The thin film is from 0.1-5.0 microns thick, optically transparent, and impermeable to water. In one embodiment, the thin film coating is silicon dioxide. In another embodiment, the spacing between the center points of two adjoining reaction chambers on the array is between 5 μm to 200 μm. Each reaction chamber has a width in at least one dimension of between 4 μm and 195 μm.

The number of reaction chambers is less than 10,000 or alternatively, the number of reaction chambers is greater than 10,000. The depth of substantially all of the reaction chambers is between 10-100 μm, preferably the depth of substantially all of the reaction chamber is 50-55 μm. In one embodiment, the reaction chambers are formed on one side of the fiber optic faceplate. In a further embodiment, the array is comprised of a surface comprising a plurality of reaction chambers and an opposed, planar, polished surface without reaction chambers, wherein the polished surface is optically transmissive such that optical signals from the reaction chambers are detected through the polished surface, wherein the distance between the surface comprising the reaction chambers and the polished surface is no greater than 5 mm in thickness.

In another embodiment, the array comprises a substrate having a surface comprising a plurality of reaction chambers and a thin film coating on said surface, wherein the thin film coating is from 0.1-5.0 microns thick and impermeable to water. In one embodiment, the thin film coating is optically transparent. In another aspect of the invention, the thin film coating is 200-400 nm thick on the surface of the substrate. In another embodiment, the thin film coating is 50-100 nm thick on the side walls of the reaction chambers, and the thin film coating is 100-300 nm thick on the bottom of the reaction chambers. Suitable arrays comprise a thin film coating that is an inorganic polymer. In a preferred embodiment, the thin film coating is silicon dioxide. The array comprises any suitable substrate. In one aspect of the invention, the substrate is a vinyl polymer, condensation polymer, copolymers and blends thereof. In one embodiment, a vinyl polymer is selected from the group consisting of polystyrene, polyethylene, polypropylene, polybutylene, polyvinyl chloride and Teflon®. In another embodiment, a condensation polymer is selected from the group consisting of polyethylene terephthalate, polyurethanes, polycarbonates, acrylics, polyamides, polyimides, polyesters and epoxies. Suitable substrates are glass, modified glass, functionalized glass, silica, silica-based materials, silicon, and modified silicon and ceramic. In a preferred embodiment, the substrate is a fiber optic faceplate.

Another embodiment of the invention comprises an array comprising a substrate having a surface with a plurality of reaction chambers, wherein said substrate is a fiber optic faceplate; and (b) an index feature. In one embodiment, the array substrate comprises side edges beveled at an angle. In a preferred embodiment, the angle is 45 degrees. A suitable index feature comprises a corner notch. In one embodiment, the substrate is marked with an identifier code. The spacing between the center points of two adjoining reaction chambers is between 5 μm to 200 μm, and each reaction chamber has a width in at least one dimension of between 4 μm and 195 μm. In one embodiment, the number of reaction chambers is less than 10,000. In another embodiment, the number of reaction chambers is greater than 10,000. The depth of substantially all of the reaction chambers is 10-100 μm, preferably the depth of substantially all of the reaction chambers is 50-55 μm. In one embodiment, the reaction chambers are formed on one side of the fiber optic faceplate. In another embodiment, the array is comprised of a surface comprising a plurality of reaction chambers and an opposed, planar, polished surface without reaction chambers, wherein the polished surface is optically transmissive such that optical signals from the reaction chambers are detected through the polished surface, wherein the distance between the surface comprising the reaction chambers and the polished surface is no greater than 5 mm in thickness.

This invention also includes a process for coating a substrate which contains a plurality of reaction chambers, wherein the coating is deposited onto the surface of the substrate using a method of deposition selected from vapor and liquid. The coating is a thin film that has a thickness of 0.1-5.0 microns, is optically transparent, and is impermeable to water. In one embodiment, the substrate is a fiber optic faceplate. In another embodiment, there are at least 10,000 reaction chambers. The depth of substantially all of the reaction chambers is 10-100 μm. In one aspect of the invention, the reaction chambers are formed on one side of the fiber optic faceplate. In another embodiment, the process is used to apply a thin film coating is silicon dioxide. Suitable thin film coatings are deposited using a vapor deposition method.

Another aspect of this invention is an apparatus for analyzing a nucleic acid sequence. The apparatus comprises: a delivery chamber, wherein the chamber comprises an array of any one of embodiments described herein; a reagent delivery device in communication with the reagent delivery chamber; an imaging system in communication with reagent delivery chamber; and a data collection system in communication with the imaging system.

This invention also includes a method for sequencing a nucleic acid, the method comprises: providing a plurality of single-stranded nucleic acid templates deposited within a plurality of reaction chambers on an array of any one of the embodiments described herein; performing a pyrophosphate sequencing reaction simultaneously on substantially all reaction chambers by annealing an effective amount of a sequencing primer to the nucleic acid templates and extending the sequencing primer with a polymerase and a predetermined nucleotide triphosphate to yield a sequencing product such that, if the predetermined nucleotide triphosphate is incorporated onto the 3' end of said sequencing primer, a sequencing reaction byproduct is produced; and identifying the sequencing reaction byproduct, thereby determining the sequence of the nucleic acid in each reaction chamber.

The present invention also includes an apparatus for etching. The apparatus is designed to produce reaction chambers on only one side of a fiber optic faceplate. The apparatus comprises at least one clamp and a gasket. The clamps are fabricated from a first acid resistant material. A clamp comprises a base having an opposed top and bottom surface, and sides and ends, and prongs. The prongs are integral with the top surface of the base. The gasket is fabricated from a second acid resistant material and comprises an index feature. A gasket has two opposing identical surfaces, a top surface and a bottom surface. In one embodiment, the first acid resistant material is poly ether ether ketone. In another embodiment, the second acid resistant material is silicone. In a suitable apparatus, the index feature of the gasket comprises a corner barrier.

This invention includes a method of etching one side of a fiber optic face plate comprising the steps of: combining two fiber optic face plates with a gasket fabricated from a second acid resistant material, wherein said gasket is positioned in between the fiber optic plates to form a sandwich; affixing clamps fabricated from a first acid resistant material, to hold the fiber optic face plates and gasket together, thereby forming a clamped sandwich having a seal that is impermeable to liquid; transferring the clamped sandwich to an acid bath for a time sufficient to form reaction chambers of the desired depth; removing the clamped sandwich from the acid bath; transferring the clamped sandwich to a first water bath; sonicating the clamped sandwich for about 5 minutes; replacing said first water bath with a second water bath; sonicating the clamped sandwich for about 5 minutes; removing the clamped sandwich from the second water bath; and detaching the clamps and gasket. Suitable methods comprise nitric acid. In one embodiment, the first acid resistant material is poly ether ether ketone and the second acid resistant material is silicone.

The present invention also includes a method of cleaning a fiber optic faceplate comprising a plurality of reaction chambers: washing the fiber optic faceplate in a solution comprising ammonium hydroxide and hydrogen peroxide; washing the fiber optic faceplate in ethylenediaminetetraacetic acid; rinsing the fiber optic faceplate in water; washing the fiber optic faceplate in a solution comprising ammonium hydroxide and hydrogen peroxide; rinsing the fiber optic faceplate in water; washing the fiber optic faceplate in ethylenediaminetetraacetic acid; rinsing the fiber optic faceplate in water; sonicating the fiber optic faceplate in a basic solution; rinsing the fiber optic faceplate in water; and repeating sonicating the fiber optic faceplate in a basic solution; rinsing the fiber optic faceplate in water. In one embodiment, the basic solution is 5% Contrad®.

BRIEF DESCRIPTION OF THE FIGURES

FIG. 1 is a series of SEM images at 5 k and 10 k magnification of etched fiber optic faceplates coated with $SiO_2$ using the sputtering (FIGS. 1a and 1b), PECVD (FIGS. 1c and 1d), and ion-plating (FIGS. 1e and 1f) vapor deposition methods;

FIG. 2 is a series of cross-sectional SEM images of fiber optic faceplates comprising reaction chambers which have been coated with $SiO_2$ showing coating thickness and quality for three vapor deposition coating methods. FIG. 2a is a schematic of a deposition area in a reaction chamber. FIG. 2b is an image of coating applied by sputtering. FIG. 2c is an image of a coating applied by PECVD. FIG. 2d is an image of a coating applied by ion-platting;

FIG. 6 is a series of Scanning Electron Micrographs of a portion of a fiber optic faceplate surface comprising reaction chambers;

FIG. 7b is a drawing of a PEEK clamp (side view);
FIG. 7c is a drawing of a PEEK clamp (front end view);
FIG. 7d is a drawing of a PEEK clamp (back end view);
FIG. 8a is a drawing of a 25×75 mm fiber optic faceplate (top view);
FIG. 8b is a drawing of a 25×75 mm fiber optic faceplate (front edge view);
FIG. 8c is a drawing of a 25×75 mm fiber optic faceplate (back edge view);
FIG. 11a is a drawing of an etch gasket (top view);
FIG. 11b is a drawing of an etch gasket (back end view);
FIG. 11c is a drawing of an etch gasket (front end view)

DETAILED DESCRIPTION OF THE INVENTION

Definitions

Figure 3:
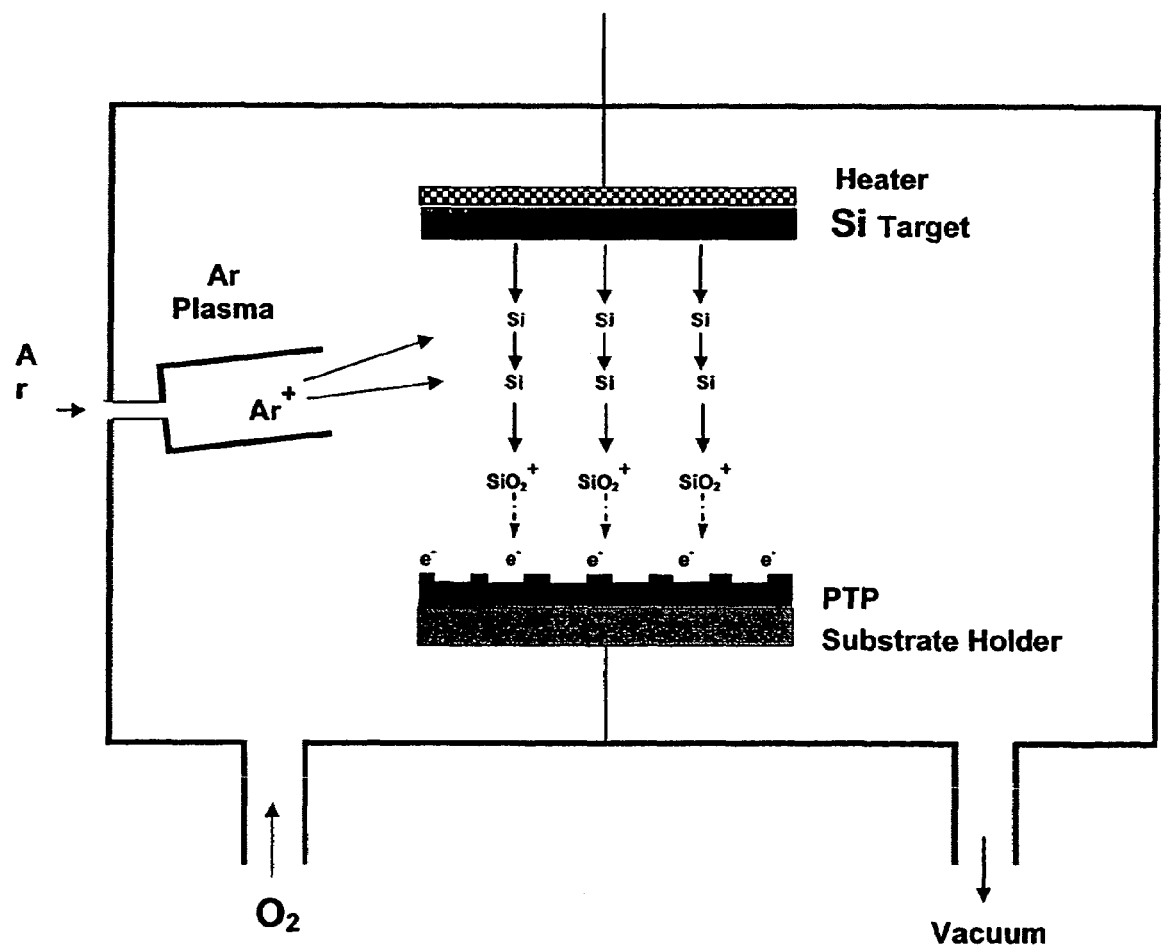
FIG. 3 is a schematic diagram of the ion-plating process.

Unless otherwise defined, all technical and scientific terms used herein have the same meaning as commonly understood by one of ordinary skill in the art to which this invention belongs. Methods and materials similar or equivalent to those described herein can be used in the practice of the present invention, and exemplified suitable methods and materials are described below. For example, methods may be described which comprise more than two steps. In such methods, not all steps may be required to achieve a defined goal and the invention envisions the use of isolated steps to achieve these discrete goals. The disclosures of all publications, patent applications, patents and other references are incorporated in toto herein by reference. In addition, the materials, methods, and examples are illustrative only and not intended to be limiting.

"Analyte" means a molecule, compound, composition or complex, either naturally occurring or synthesized, to be detected or measured in or separated from a sample of interest. Analytes include, without limitation, proteins, peptides, amino acids, fatty acids, nucleic acids, carbohydrates, hormones, steroids, compounds, lipids, vitamins, bacteria, viruses, pharmaceuticals, and metabolites.

"Clamped Sandwich" refers to a combination of two FOFs with a gasket positioned in between the two FOFs, wherein the corner notch of each FOF is properly aligned with the appropriate gasket corner barrier, such that the polished surface of each FOF is facing towards the gasket, wherein a seal is formed between the polished surface of the FOF and the gasket which is impermeable to liquid.

"Core material" refers to the inner component of a fiber optic fiber. The material is transparent and has a high refractive index.

"Cladding material" refers to the outer component of a fiber optic fiber. The material is transparent and has a low refractive index.

"Corner barrier" refers to a feature on a gasket, which includes a band that is placed at an angle in the corner of a gasket and provides a physical basis for orienting an FOF when the FOF is mounted in the gasket.

"Corner notch" refers to one corner of a fiber optic faceplate which is cut at angle and removed to provide a physical basis for orienting the fiber optic faceplate, for example when a fiber optic faceplate is mounted on a system for analysis or in a gasket for the etch process, the corner notch of the fiber optic faceplate is matched with a complementary feature located on the analysis system or gasket.

"Etch process" refers to a chemical process using acid to create reaction chambers in an array substrate.

"Fiber optic faceplate" or "FOF" refers to a bundle of fiber optic cables which are fused together to form a monolithic structure which is then "sliced" and polished to form a "wafer" of required thickness.

"Functional groups" means any chemical or biological species capable of affixing a reactant or analyte to the inside surface of the reaction chamber.

"Gasket" refers to one component of the apparatus for the etch process. The gasket is aligned between two FOFs and protects one side of each FOF (e.g., the polished side) from exposure to acid by forming a fluid tight seal.

"Gasket Index Feature" refers to a band positioned in one corner of a gasket which creates a notch that is complementary to the corner notch of a FOF and that provides a physical basis for orienting a FOF.

"Index Feature" refers to a structure that provides a physical basis for orienting a FOF.

"FOF Index Feature" refers to a corner notch on the FOF which provides a physical basis for properly orienting a FOF.

"Ion-Plating" means a method of vapor deposition used for depositing a thin film coating on an array substrate.

"Impermeable to water" refers to the ability of a thin film to provide a barrier to an aqueous solution contained in the reaction chamber and to prevent leaching of the chamber solution into the wall components of the reaction chamber.

"Optically transparent" refers to the ability of light to transmit through a material.

"PEEK clamp" refers to a clamp made of poly ether ether ketone which is used to firmly hold two FOFs and a gasket together during the etch process.

"PicoTiter Plate™" or "PTP" means an array substrate comprising an etched FOF.

"Plasma-Enhanced Chemical Vapor Deposition" or "(PECVD)" means a method of vapor deposition used for depositing a thin film coating on an array substrate.

"Reactant" means any chemical or biological molecule, compound, composition or complex, either naturally occurring or synthesized, that is capable of binding, forming, or reacting with an analyte in a sample of interest either alone or in conjunction with another reactant. The reactants of the present invention are useful for chemical reaction or biochemical measurement, detection or separation. Examples of reactants include, without limitation, amino acids, nucleic acids, including oligonucleotides and cDNA, carbohydrates, and proteins such as enzymes and antibodies.

"Reaction Chamber" means a localized well or chamber (i.e. a hollowed-out space, having width and depth) on a substrate, comprising side walls and a bottom that is used to facilitate the interaction of reactants.

"RCA cleaner" means a solution of ammonium hydroxide and hydrogen peroxide.

"RER cleaning process" refers to a process for cleaning an etched FOF using RCA cleaner, EDTA, and RCA cleaner.

"Sandwich" refers to a combination of two FOFs with a gasket positioned in between the two FOFs, wherein the corner notch of each FOF is properly aligned with the appropriate gasket index feature, such that the polished surface of each FOF is facing towards the gasket and the unpolished surface is exposed.

"Scanning Electron Microscopy" or "SEM" refers to a method for high resolution imaging.

"Sputtering" means a method of vapor deposition used for depositing a thin film coating on an array substrate.

"Substrate" refers to a solid support or any material that can be modified to contain discrete individual reaction chambers and is amenable to at least one detection method.

"Thin film" refers to the coating of material deposited on the surface of the substrate less than 5.0 microns thick.

"Vapor deposition" refers to a method for depositing a thin film coating on the array.

The present invention provides array compositions comprised of a substrate containing individual reaction chambers and coated with a thin film. The invention includes the process of fabricating the array including methods of depositing the thin film coating, etching, cleaning and using the array. The invention also includes hardware used in the etching process. By "array" herein is meant a plurality of reaction chambers, which are localized wells or chambers in an array format on the substrate material; the size of the array and its reaction chambers will depend on the composition and end use of the array. The surface of the array substrate is coated with a thin film to enhance the properties and functions of the reaction chambers. The thin film coating protects the contents of the solution in the reaction chamber from the deleterious effects of the array substrate, without compromising the utility or ease of fabrication of the array. The thin film also provides a uniform surface composition allowing for uniform modification of the reaction chamber surface (e.g., with a monolayer).

The invention described herein can be a component of a larger system and methods. Such system and methods can be used to process nucleic acids in a multitude of ways. For example, methods are performed to determine the identity of a sequence of nucleic acids, or for single nucleotide polymorphism (SNP) detection in nucleic acid fragments, for nucleic acid expression profiling (comparing the nucleic acid expression profile between two or more states e.g., comparing between diseased and normal tissue or comparing between untreated tissue and tissue treated with drug, enzymes, radiation or chemical treatment), for haplotying (comparing genes or variations in genes on each of the two alleles present in a human subject), for karyotyping (diagnostically comparing one or more genes in a test tissue, typically from an embryo or fetus prior to conception to detect birth defects, with the same genes from "normal" karyotyped subjects), and for genotyping (comparing one or more genes in a first individual of a species with the same genes in other individuals of the same species).

A typical analytical system has a number of components. These include, for example, (1) a nucleic acid template that is to be processed, (2) a delivery chamber, wherein the chamber comprises a thin film coated array of the invention, an apparatus for containing the nucleic acid template, (3) a flow chamber and reagent delivery means that permits flow of nucleic acid processing reagents over the nucleic acid template where the assay reagents generate a detectable signal, e.g., light, as the nucleic acid is processed, (4) an imaging system in communication with the reagent delivery chamber that detects the signal emitted as the nucleic acid is processed and that converts the captured light into data, and (5) a data collection system in communication with the reagent delivery chamber that processes the data to yield meaningful information about the nucleic acid that has been processed.

1. Thin Film Coated Arrays

The present invention includes an array comprising a substrate with a plurality of reaction chambers, and a thin film coating on said surface of the substrate, wherein the film is from 0.1-5.0 microns thick and impermeable to water.

A. The Array Substrate

The array substrate is the solid support that can be modified to contain individual reaction chambers. Any material is used as the substrate. Substrate materials include, but are not limited to, organic polymers and plastics, such as vinyl polymers including polystyrene, polyethylene, polypropylene, polybutylene, polyvinyl chloride, and Teflon®, including copolymers and blends, as well as condensation polymers including polyethylene terephthalate, polyurethanes, polycarbonates, acrylics, polyamides, polyimides, polyesters, and epoxies, and silicones including copolymers and blends. Substrate materials may also include inorganic materials including ceramics, glasses, modified or functionalized glasses, silica or silica-based materials, silicon and modified silicon. Substrate materials may also comprise fiber optic bundles. In general, all of these types of materials are easily formed into arrays containing reaction chambers. However, arrays made from such materials are often incompatible with many organic solvents and thus, applying a thin film coating to such an array enhances the solvent compatibility of the array.

Generally, the substrate is planar (flat), although other configurations of substrates are used; for example, substrates are concave, convex, three-dimensional, e.g. spherical, textured, or cavitated, e.g., in a cavitated terminus of a fiber optic fiber or in a microwell etched, molded, or otherwise micromachined into the planar surface, e.g. using techniques commonly used in the construction of microelectromechanical systems. See e.g., Rai-Choudhury, HANDBOOK OF MICROLITHOGRAPHY, MICROMACHING, AND MICROFABRICATION, VOLUME I: MICROLITHOGRAPHY, Volume PM39, SPIE Press (1997); Madou, CRC Press (1997), Aoki, Biotech. Histochem. 67: 98-9 (1992); Kane et al., Biomaterials. 20: 2363-76 (1999); Deng et al., Anal. Chem. 72:3176-80 (2000); Zhu et al., Nat. Genet. 26:283-9 (2000). In a preferred embodiment, the substrate is planar.

In general, the substrate allows optical detection and does not itself appreciably fluoresce. The substrate is preferably made of a material that facilitates detection of the chemical reaction event or assay result. For example, in a typical nucleic acid sequencing reaction, binding of a dNTP to a sample nucleic acid to be sequenced can be monitored by detection of photons generated by enzyme action on phosphate liberated in the sequencing reaction. Thus, having the substrate made of a transparent or light conductive material facilitates detection of the photons. In some embodiments, the substrate is optically transparent. In a preferred embodiment, the surface of the substrate can be optically interrogated.

1. Fiber Optic Faceplate ("FOF")

In a preferred embodiment, the substrate of the array is fashioned from a "sliced" fiber optic bundle or a fiber optic faceplate ("FOF"). A FOF is fabricated by fusing many optical fibers together into a monolithic structure (i.e. a bundle) which retains the light transmission properties of the individual fibers. A fiber bundle is "sliced" to form a "wafer," a FOF. The resulting FOF possesses similar handling properties to that of a plane of glass or microscope slide. A FOF is a substrate onto which wells or chambers are etched to create an array of reaction chambers.

The individual fiber optic fibers comprising a FOF are composed of two materials, an inner "core" material and an outer layer "cladding" material (FIG. 2). The fiber optic core consists of a material which is transparent and has a high refractive index. Examples of core materials include heavy metal oxides such as lead, barium, lanthanum, and niobium oxides. The fiber optic cladding consists of a material which is transparent and has a low refractive index. One typical cladding material is doped silicon dioxide. Doping agents include metal oxides, such as boron, and aluminum.

The individual fibers comprising a FOF each have a diameter. The individual fibers are any size in diameter (e.g., 3 µm to 100 µm). In one embodiment, the individual fibers are 6 µm to 12 µm in diameter. Once a fiber optic bundle has been fused to form a monolithic structure, the fibers are not individually manipulated; that is, one strand generally cannot be physically separated at any point along its length from another fiber strand. Fused fiber optic bundles and face plates are obtained commercially from manufacturers.

One surface of a FOF (i.e., the non-reaction chamber side) is typically highly polished so as to allow optical-coupling (e.g., by immersion optic or other optical coupling fluids) to a detection device (FIG. 2). In one embodiment, optical-coupling may be facilitated by a second fused fiber bundle. This second fused fiber bundle typically has a significantly smaller fiber size than the first FOF containing the reaction chambers, and serves to act as a conduit for the transmission of light product to the attached detection device, such as a CCD imaging system or camera.

In a preferred embodiment, the array substrate comprises a FOF. The overall shape of a FOF is rectangular, although it is understood by those skilled in the art that a FOF is not limited to a specific shape and suitable FOFs include a variety of other shapes and overall dimensions. A FOF has at least a top and bottom surface which are opposed, wherein there is a distance between the top surface and the bottom surface. The fibers within the FOF are oriented substantially perpendicular to said top and bottom surfaces. A FOF further includes at least one index feature to provide a physical basis for ensuring proper orientation of a FOF in both automated equipment and for manual processes. For example, an index feature is used to properly position a FOF in the instrument for analysis.

FIGS. 8a-8c illustrate a FOF 1 for use with this invention. In one embodiment, a FOF 1 has a planar top surface 2 and a planar bottom surface 3, which are opposed. A FOF 1 is optically conductive such that optical signals from the reaction chambers are detected through the bottom planar surface 3, wherein there is a distance $D_1$ between the top surface and the bottom surface. The distance $D_1$ can be any distance. In one embodiment, typically the distance $D_1$ between the top surface 2 and the bottom surface 3 is no greater than 10 cm, preferably no greater than 5 mm. In another embodiment, $D_1$ is between 0.5 mm to 5 mm, most preferably about 2 mm. The top surface 2 and bottom surface 3 of a FOF 1 are polished or alternatively non-polished. Preferably, one surface is polished and the opposing surface is non-polished. In one aspect of this invention, the top surface 2 is polished and the bottom surface 3 is non-polished. In a further embodiment, the top surface 2 is polished and the bottom surface 3 comprises reaction chambers.

A FOF 1 has at least a first and second side and at least a first and second end. In one embodiment, a FOF 1 has a first end 4 and a second end 5 separated by a distance; a first side 6 and a second side 7 separated by a distance; and one corner side 8 extending between an end and a side. In one embodiment, shown in FIG. 8a, a corner edge 8 extends between a second side 7 and a second end 5. The ends and sides are connected to form the outer perimeter of a FOF 1. For example, a first side 6 and the second side 7 both extend perpendicularly between the first and second ends 4, 5.

The sides and/or ends of an FOF may be beveled at an angle in order to make it possible for the FOF to be mounted in an instrument. Any combination of sides and ends are beveled or alternatively, none of the sides or ends are beveled. In one embodiment, all of the sides and ends are beveled at an angle. A beveled side edge is beveled at an angle to form an inclined portion and a flat portion or alternatively, the beveled side has no flat portion. In one preferred embodiment, the first side 6 is beveled at an angle $A_1$ to form an angled first side edge 17. The angled first side edge 17 is formed by an incline portion 15 and a flat portion 12. The flat portion 12 of the angled first side 17 has a height of $L_8$. Similarly, the second side 7 is beveled at an angle to form an angled second side edge 16. The first and second side edges 6 and 7 are beveled to any angle. In one embodiment, the side edges are beveled to an angle between 10 and 80 degrees. In another embodiment, the angle is substantially 45 degrees, wherein substantially means that the angle a little more or a little less than 45 degrees. In one aspect of the invention, the opposing side edges are beveled to allow the FOF to slide into a suitable retaining structure (e.g., a cartridge) located inside the analytical instrument that will capture and properly locate and mount the FOF relative to the fluidic reaction chamber and the camera.

In a preferred embodiment, the first and second sides 6 and 7 are each beveled to form a 45 degree angle and the length $L_8$ of the resulting flat portion is 0.20 mm-0.45 mm. The beveled sides are located along the planar optically conductive bottom surface.

Those of ordinary skill in the art will appreciate that the top surface and bottom surface of a FOF can be any length and any width. In one embodiment, the length and width are the same. In embodiments where at least one of the sides is beveled, the width of the top surface is slightly smaller than the width of the bottom surface due to the angled side edge. For example, in one embodiment the width $W_2$ of the top surface 2 is about 38 mm and the width $W_3$ of the bottom surface 3 is about 40 mm. In similar embodiments where at least one of the ends is beveled, the length of the top surface is slightly smaller than the length of the bottom surface.

In a first embodiment, bottom surface 3 has a length $L_3$ of about 75 mm, the width $W_3$ of the bottom surface 3 is about 40 mm. The top surface 2 has the same length $L_3$ as the bottom surface 3 and the width $W_2$ of the top surface 2 is about 38 mm.

In a second embodiment, bottom surface 3 has a length $L_3$ of about 75 mm, the width $W_3$ top surface 2 is about 25 mm. The top surface 2 has the same length $L_3$ as bottom surface 3 and the width $W_2$ of the top surface 2 is about 22 mm.

Suitable FOFs may include, for example, one or more index features. An index feature is located anywhere on a FOF and is not limited to any specific shape or size. An index feature is preferably located on the perimeter of the FOF and preferably in a corner. The purpose of an index feature is to provide a physical basis to allow engagement of a FOF to ensure its proper orientation. As shown in FIG. 8a, a suitable FOF 1 includes an index feature that is a corner notch 13 formed by removing a portion of the corner of the FOF where a side and end of the FOF connect perpendicularly. A FOF 1 has one or more corner notches. In a preferred embodiment, a FOF 1 has one corner notch 13. In a more preferred embodiment, one corner notch 13 is formed by removing the corner, where the second side 7 connects the second end 5. The corner portion is cut off at an angle $A_2$ to create a corner notch 13. An angle $A_2$ is not limited to a particular degree and includes other angles and shapes. In a preferred embodiment, an angle $A_2$ is removed from the corner portion of FOF 1 where the second side 7 connects to the second end 5 and the angle $A_2$ is about 45 degrees. The resulting corner side 8 has a length $L_{11}$ which is any length. In a preferred embodiment, $L_{11}$ is about 6 mm. The corner notch 13 is matched with a complementary feature designed into the component in which a FOF 1 fits e.g., a feature designed into the FOF mounting hardware of the analysis system or a feature designed into a gasket of an etching apparatus.

A FOF 1 may be labeled with one or more identifier codes. A FOF is marked with an identifier code for a variety of purposes. For example, an identifier code enables tracking and/or authenticating of a FOF. An identifier code also allows visual orientation of a FOF 1 when it is mounted in the analysis system (i.e., the system does not operate to analyze a FOF 1, unless the analysis system can properly read the identifier code). The identifier code may be any type of code e.g., a bar-code, a two dimensional bar-code such as a Data Matrix code, etc. In one embodiment, a FOF 1 is coded with a bar-code. In another embodiment, a FOF 1 is coded with a Data Matrix code. In a preferred embodiment, a FOF 1 has both a bar-code and Data Matrix code. An alpha-numeric code that can be read by a human may also be incorporated. The identifier code can be read by an instrument, for example, a CCD camera, or a bar-code reader.

In one embodiment, an identifier code may be directly etched into the FOF surface with a laser. In and alternative embodiment, the identifier code is printed onto the surface of the FOF.

B. The Array Surface

Prior to coating with the thin film, at least one surface of the substrate is modified to contain one or more individual reaction chambers, arranged so as to allow for the discrete localization of each reaction mixture or assay solution in a defined space, as well as for detection of the analytical result. Thus, as used herein, the term "reaction chamber" refers to a localized "well" or "chamber" on the substrate that facilitates interaction of reactants, e.g., in a nucleic acid sequencing reaction. Typically, the reactants are distributed into the reaction chamber in a medium which facilitates the chemical reaction or bioassay and which flows through the reaction chamber. For example, for DNA sequencing, the nucleic acid template is distributed into the reaction chamber on one or more solid supports or beads in a solution which flows through the reaction chamber.

In one aspect of this invention, the surface of the substrate is modified to contain a plurality of reaction chambers. In a preferred embodiment, the reaction chambers are located on the bottom surface 3 of the FOF (FIGS. 8a and 8b). The reaction chambers are preferably located in zone 1 of the FOF (FIG. 8a).

The reaction chambers on the array surface typically take the form of wells or chambers in the substrate having side walls and a bottom and both width and depth, into which reaction mixtures or assay solutions can be deposited (FIG. 2). The reaction chambers are preferably of sufficient dimension and order to allow for (i) the introduction of the necessary reactants into the chambers, (ii) chemical reactions or bioassays to take place within the chamber and (iii) inhibition of mixing of reactants and/or analytes between chambers. The reaction chamber can be any shape. In one embodiment, the shape of the reaction chamber is preferably circular or cylindrical, but can be multi-sided so as to approximate a circular or cylindrical shape. Referring to FIG. 6, the shape of the reaction chamber in a preferred embodiment is substantially hexagonal. The chamber can have a smooth wall surface. In an additional embodiment, the chamber can have at least one irregular wall surface. The bottom of the reaction chambers can be either planar or concave or convex.

The reaction chambers can be in a pattern, i.e. a regular design or configuration, or the chambers can be randomly distributed on the array surface. In one embodiment, there is a regular pattern of reaction chambers such that the chambers may be addressed in the X-Y coordinate plane. "Pattern" in this sense includes a repeating unit, preferably one that allows a high density of chambers on the substrate. In a preferred embodiment, an irregular hexagonal packed array of reaction chambers is on the surface of the array substrate as illustrated by FIG. 6.

The reaction chambers may be spaced any suitable distance apart. Spacing is determined by measuring the distance between the center points of two adjoining reaction chambers (FIG. 2). The reaction chambers are generally spaced between 5 μm and 200 μm apart. The reaction chambers may be spaced 10 μm and 150 μm apart, and preferably between 20 μm and 100 μm apart, and most preferably between 40 and 60 μm apart. In a preferred embodiment, the reaction chambers have a spacing between the center points of two adjoining chambers of about 43 μm to 50 μm. The size of the reaction chamber can be made to accommodate any volume. In a preferred embodiment, the chamber volume is between 10 to 150 pL, preferably between 20 to 90 pL, more preferably between 40 to 85 pL, and most preferably about 75 pL.

The reaction chambers may have any suitable width. In one embodiment, the reaction chambers have a diameter (width) in one dimension of between 3 μm and 100 μm, preferably 20 μm and 70 μm and more preferably about 30 μm and 50 μm. In a most preferred embodiment, a reaction chamber has a diameter of 38 μm to 44 μm.

The reaction chambers may have any suitable depth. The depth of substantially all of the reaction chambers is generally 10 μm and 100 μm, and preferably 20 μm and 60 μm. In a more preferred embodiment, the depth of substantially all of the reaction chambers is 50-55 μm. Alternatively, substantially all of the reaction chambers have a depth that is between 0.25 and 5 times the width in one dimension of the reaction chamber or, in another embodiment, between 0.3 and 1 times the width in one dimension of the reaction chamber. Substantially all of the reaction chambers means at least 90% of the reaction chambers. In another embodiment, substantially all of the reaction chambers means at least 95%, more preferably 97%. In a further embodiment, substantially all of the reaction chambers means at least 99%, more preferable all of the reaction chambers. In a preferred embodiment, the reaction chamber ranges in depth on a FOF from approximately one-half the diameter of an individual optical fiber up to two to three times the diameter of the fiber. The depth of a reaction chamber is measured, for example using a MicroXam 3-D interferometric surface profiler (ADE Phase shift, San Jose, Calif.). Routine reaction chamber depth measurements can be made using the area difference plot feature of the instrument. The instrument compares the depth of eight chambers to a reference point on the FOF cladding to provide an average chamber depth.

The array preferably comprises a sufficient number of reaction chambers to carry out such numerous individual assays. The array contains any number of reaction chambers. Depending on the end use of the array, substrates are made to contain a very high density (e.g., greater than 200,000), high density (e.g., at least 100,000), moderate density (e.g., at least 50,000), low density (e.g., at least 10,000), and very low density (e.g., less than 10,000) of reaction chambers. Low density arrays have a small number of reaction chambers. In one embodiment there are less than 10,000 reaction chambers. For example, the array contains 1-96 reaction chambers. In one embodiment, the array contains 96-384 reaction chambers. In another embodiment, the array contains 384-1536 reaction chambers. In a further embodiment, the array contains greater than 1536 reaction chambers.

In one aspect of the invention, a FOF is made to contain a very large number of reaction chambers. In one embodiment, there are at least 10,000 reaction chambers, preferably at least 50,000 reaction chambers, more preferably greater than 100,000 reaction chambers, and even more preferably greater than 200,000 reaction chambers on the surface of the substrate. Since the number of simultaneous analytical measurements is limited by the number of reaction chambers, the throughput of analytical measurement performed using an array may be increased by fabricating array substrates containing increasing densities of reaction chambers. Table 1 shows this progression for a 14×43 mm and 30×60 mm active areas, derived from 25×75 mm and 40×75 mm FOFs, respectively. See, for example, co-pending U.S. patent application Ser. No. 10/767,779, herein incorporated by reference. Pitch is the distance between fibers, measured 'center to center' (Table 1). Pitch and fiber size are generally equivalent.

TABLE 1

Development of arrays with a higher number of reaction chambers.

| Pitch (um) | Reaction Chamber Diameter (um) | # of Reaction Chambers (14 × 43 mm) | # of Reaction Chambers (30 × 60 mm) |
|---|---|---|---|
| 50 | 44 | 275K | 800K |
| 43 | 38 | 375K | 1.2 M |
| 35 | 31 | 575K | 1.6 M |
| 25 | 22 | 1.1 M | 3.2 M |

As illustrated above, one particular advantage of the present invention is that, particularly through the use of fiber optic technology, improved extremely high density arrays can be made. Thus, for example, it can be possible to have as many as 50,000 different fibers and cells in a 1 mm$^2$ fiber optic bundle, with densities of greater than 250,000 individual fibers per 0.5 cm$^2$ obtainable.

For example, a wide channel reaction chamber can have dimensions of approximately 14 mm×43 mm. Thus, with this approximate dimension and at approximately $4.82 \times 10^{-4}$ chambers/um$^2$ density, the array can have approximately 290,000 fluid accessible reaction chambers.

Reaction chambers are formed in the surface of the substrate as is generally known in the art using a variety of techniques, including but not limited to, chemical etching, photolithography, stamping techniques, pressing, casting, molding, microetching, electrolytic deposition, chemical or physical vapor deposition employing masks or templates, electrochemical machining, laser machining or ablation, electron beam machining or ablation, and conventional machining. The technique will depend on the composition and shape of the substrate. In a preferred embodiment, reaction chambers are formed using chemical etching. Reaction chambers are typically formed in the substrate prior to coating the array with the thin film coating.

C. The Thin Film Coating

The present invention provides for the application of a thin film coating to the array substrate. Such thin film coating is designed to improve the properties and functions of the array, including compatibility of the reaction mixture or assay solution with the array substrate. The film provides a barrier between the solution contained in the reaction chamber and the substrate, and prevents both leaching of the substrate material into the solution and contact of the contents in the reaction chamber with the substrate.

In a preferred embodiment, the substrate of the array is coated with a thin film comprised of a material typically known to be compatible with components found in assay solutions and chemical reaction mixtures. In one embodiment, the thin film coating is impermeable to water. In another embodiment, the thin film coating provides for a uniform surface composition. Preferably, the thin film coating is optically transparent and such transparency facilitates detection. Other desirable properties of the thin film coating include durability, compatibility with the substrate materials, well-understood deposition parameters, and resistance to high temperatures. In one embodiment, the thin film coating is adhesive to glassy materials. The thin film preferably minimizes non-specific absorption of macromolecules to the walls and bottom of the reaction chamber. In one embodiment, the thin film coating allows for easy attachment of reactants (e.g. proteins and nucleic acids) and does not negatively affect the activity of immobilized reactants, but rather in some instances, can increase their stability.

The array substrate may be coated in its entirety or the thin film coating may be deposited on the surface of the array, the bottom and/or on the side walls of each reaction chamber (FIG. 2). In one embodiment, the thin film is deposited on the entire array substrate. In another embodiment, the thin film is deposited on the surface of the array. In a further embodiment, the thin film is deposited on the bottom of each reaction chamber. In a further embodiment, the thin film is deposited on the side walls of each reaction chamber. In a more preferred embodiment, the thin film is deposited on the bottom and side walls of each reaction chamber and the surface of the array. The term "thin film" refers to a film with a thickness that is significantly smaller than other characteristic dimensions of the array. In a preferred embodiment, the thickness of the thin film coating is from 0.1-5.0 microns. The thickness of the thin film may be non-uniform over the surface of the array. For example, in one embodiment, the thickness of the thin film coating is approximately 200-400 nm on the top surface of the array substrate; 50-100 nm on the side walls of the reaction chambers, and 100-300 nm on the bottoms of the reaction chambers.

Many different types of materials are used as a thin film. The composition of a thin film material will depend on the array substrate, the application, and the method of thin film deposition. In one embodiment, a thin film coating is a polymer. In a preferred invention, the polymer is an inorganic polymer. A thin film coating can be a non-metal oxide (e.g. silicon dioxide ($SiO_2$)). Other thin film coatings are, for example, a metal alloy, a metal or semi-conductor oxide, nitride, carbide or boride. Other materials for coating the substrate include gold layers, e.g. 24 karat gold. Many thin film coatings are commercially available.

Coating materials also include those systems used to attach an anchor primer to a substrate. Organosilane reagents, which allow for direct covalent coupling of proteins via amino, sulfhydryl or carboxyl groups, can also be used to coat the array substrate. Additional coating substances include photoreactive linkers, e.g. photobiotin, (Amos et al., "Biomaterial Surface Modification Using Photochemical Coupling Technology," in *Encyclopedic Handbook of Biomaterials and Bioengineering, Part A: Materials*, Wise et al. (eds.), New York, Marcel Dekker, pp. 895926, 1995).

Other coating materials include polymeric materials such as hydrophilic polymer gels such as polyacrylamide and polysaccharides, which preferably are polymerized directly on the surface of the substrate or polymer chains that are covalently attached to the substrate directly (Hjerten, *J. Chromatogr.* 347,191 (1985); Novotny, *Anal. Chem.* 62,2478 (1990), as well as pluronic polymers (triblock copolymers, e.g. PPO-PEO-PPO, also known as F-108), specifically adsorbed to either polystyrene or silanized glass surfaces (Ho et al., *Langmuir* 14:3889-94, 1998), as well as passively adsorbed layers of biotin-binding proteins. The surface can also be coated with an epoxide which allows the coupling of reagents via an amine linkage.

In a preferred embodiment, the thin film coating is $SiO_2$. Immediately prior to applying the thin film coating, the FOFs are cleaned by sonication in a 5% Contrad® solution. The 5% Contrad® solution consists of substantially 5 percent Contrad®. Substantially 5% means that the solution may be a little more or a little less than 5% Contrad®. After cleaning, an ion-plating process is used to coat the etched FOFs with a thin film coating of $SiO_2$, wherein the thickness of the thin film is from 0.1-5.0 microns. In one embodiment, the thickness of the thin film coating is 200-400 nm on the surface of the fiber optic faceplate. In another embodiment, the thickness of the thin film coating is 50-100 nm on the side walls and is 100-300 nm on the bottom of the reaction chamber. $SiO_2$ is transparent, has a very efficient water barrier thicknesses down to 10 nm, adheres to glassy materials, and withstands harsh cleaning procedures and high temperatures. Further, the surface properties of $SiO_2$ are well known, as are methods for modifying these properties. Further, $SiO_2$ has also been shown to be compatible with microscale polymerase chain reaction ("PCR) conditions.

Generally, the reactants and analytes are non-covalently associated in the reaction chambers. However, the thin film coated chambers can be biologically or chemically functionalized. Any of the thin film materials discussed can be derivatized with one or more functional groups, commonly known in the art for the immobilization of enzymes and nucleotides, e.g. metal chelating groups (e.g. nitrilo, triacetic acid, iminodiacetic acid, pentadentate chelator). In one embodiment, the thin film coated chamber is modified to contain functional groups that can be used to attach or capture, either covalently or non-covalently, reactants or analytes to the thin film coated walls and/or bottom of the reaction chamber. "Chemically modified reaction chambers" in this context include, but are not limited to, the addition of functional groups including amino groups, carboxy groups, oxo groups and thiol groups, that can be attached to the reaction chamber thin film coated surface and used to attach or capture reactants or analytes on the same surface. Alternatively, biological modifications of the film coated chamber include the attachment of binding ligands or binding partner pairs, including but not limited to, antigen/antibody pairs, enzyme/substrate or inhibitor pairs, receptor-ligand pairs, carbohydrates and their binding partners (lectins, etc.).

2. Process for Single Sided Chemical Etching of a Fiber Optic Faceplate

The present invention is further directed to a process for producing reaction chambers on an array substrate and an apparatus for performing such a process. In one embodiment, reaction chambers are formed on a FOF substrate. In a preferred embodiment, reaction chambers are formed using a selective chemical etching process which takes advantage of the difference in etch rates between core and cladding materials. See, e.g., Pantano, et al., *Chem. Mater.* 8:2832 (1996), and Walt, et al., U.S. Patent Publication No. 20020015146. Reaction chambers may be formed on one or both sides of a FOF. Methods for forming reaction chambers on both sides of the substrate require no special hardware or an apparatus beyond an etching bath. However, the reaction chambers etched on one of the side of the FOF subsequently need to be removed so that the surface will be smooth enough for optical coupling to a camera system. This removal process involves an expensive and time-consuming polishing step. If reaction chambers are formed only on a single side, the FOF is almost immediately ready for cleaning and surface coating. The present invention provides a both an apparatus and a chemical etching process which are designed to produce reaction chambers on only one side of a FOF.

A. Etch Apparatus: Clamps and Gasket

Figure 12:
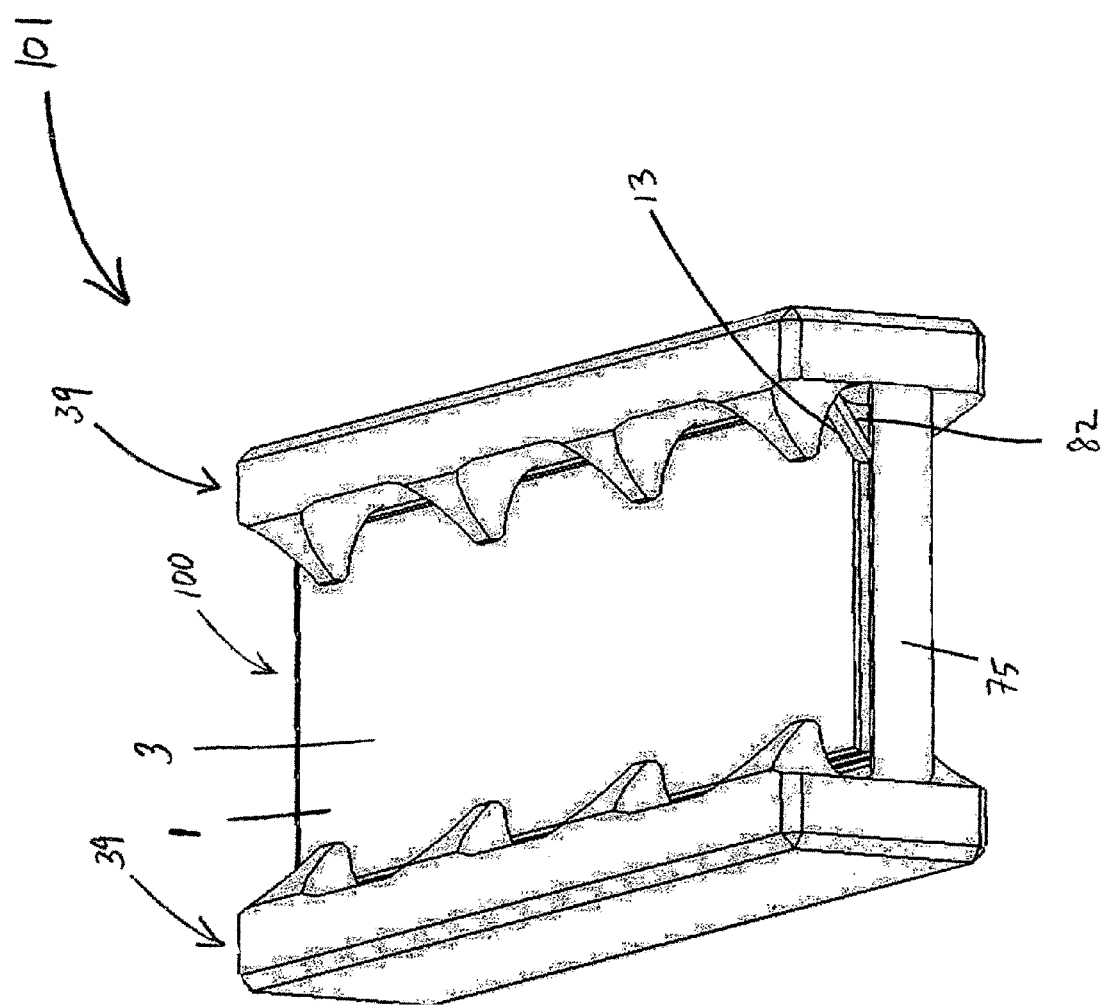
FIG. 12 is a drawing of an assembled fiber optic faceplate "clamped sandwich" held together with two clamps and ready for the etch process (top view)
Figure 13:
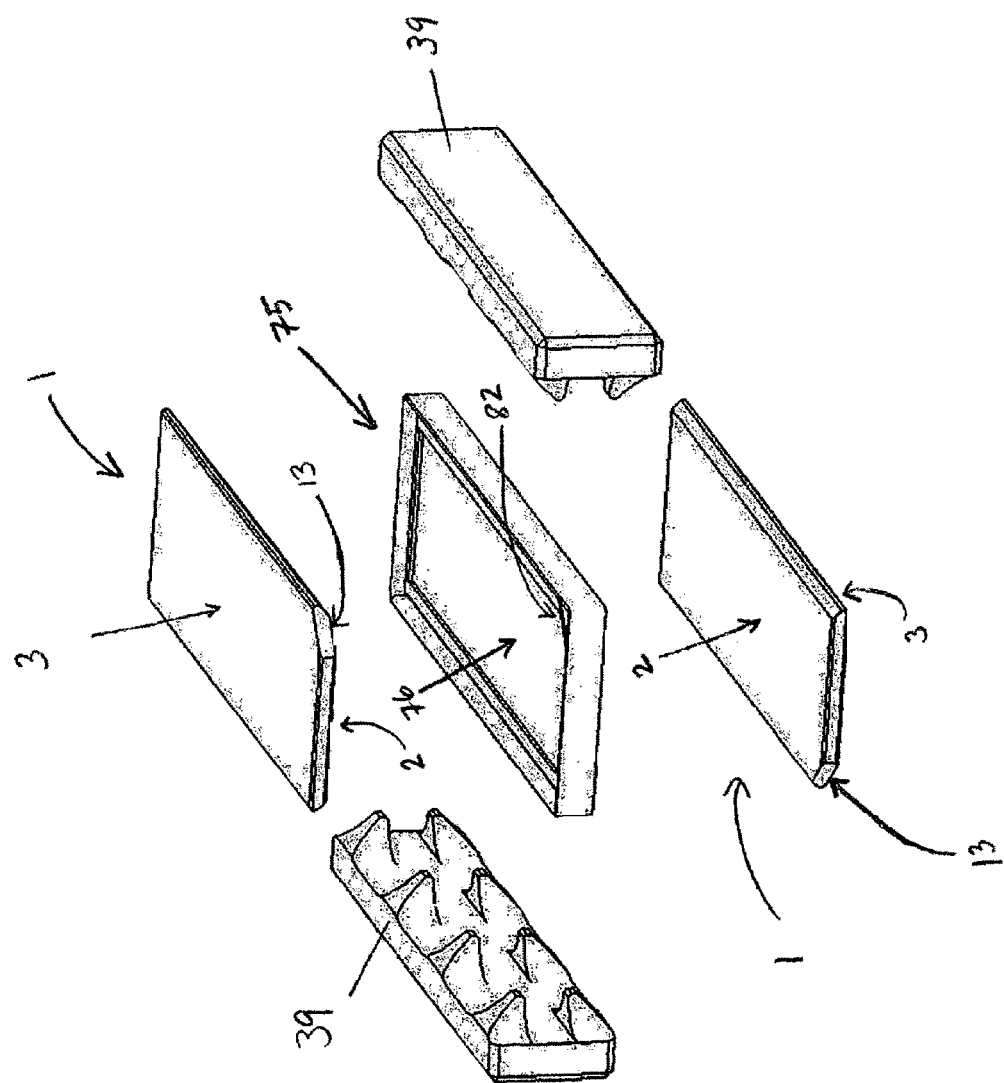
FIG. 13 is an exploded view drawing of a fiber optic faceplate "clamped sandwich".

Generally, an apparatus used to etch a FOF on a single side includes the following pieces of hardware: at least one clamp and a gasket (FIGS. 12 and 13). The term "sandwich" refers to two FOFs with a gasket positioned in between the two FOFs. A clamp 39 is a device which is used to press or hold firmly the two FOFs 1 together with a gasket 75 to form a "clamped sandwich" which is used during the etch process. A gasket 75 is designed to create a fluid tight seal in a clamped sandwich, e.g., a gasket is placed in between two FOFs in order to protect one side of each FOF from exposure to acid. Both the FOFs and gasket each contain an index feature which provides a physical basis for mounting the FOFs so that only one side of each FOF is subjected to acid treatment.

1. Clamp

The present invention comprises a clamp which includes two joined components, a base and prongs. Both components are constructed from a single suitable material, or alternatively, each component is constructed separately from suitable materials and mated together using any variety of mating techniques known in the art (e.g., adhesively attached, mechanically mated etc.). A base is generally the shape of a rectangular box having at least a top surface and a bottom surface which are opposed, wherein there is a distance between the top and bottom surface. A bottom surface is permanently joined to a top surface by sides and ends which are permanently joined to form the outer perimeter of the base. A base has at least a first and second side and at least a first and second end. A surface of a base is generally planar.

At least two prongs are aligned on a surface of a base. In this version of the invention, at least two prongs are aligned on a top surface of a base and extend radially outward a distance. Any number of prongs are aligned on a top surface. A suitable prong is any shape or size. For example, a prong is a tapered rectangle having at least four edges, including an external and internal edge and a first and second edge. External and internal edges are opposed and first and second edges are opposed. The edges of a prong are connected to form a tapered rectangular shaped prong. An internal edge of a prong is flat and attaches perpendicularly to a top surface of a base. A prong has a top and a height. A pair of prongs is positioned along a top surface, with the internal edge of one prong opposed to the internal edge of a second prong to form a slot down the middle of the top surface of a base. A slot with a width $W_{11}$ is where FOFs and a gasket are securely held by the prongs of a clamp. It is understood by those in the art that a clamp is not limited to a specific shape and includes other shapes and overall dimensions.

Referring to FIGS. 7a-d, one embodiment of the invention includes a unitary clamp 39 comprised of a rectangular shaped base 40 and at least two prongs 43, 44. A base has a top surface 41 and a bottom surface 42, which are opposed. A bottom surface 42 is permanently joined to a top surface 41 by any number of sides and ends, which are connected to form the outer boundary of a base 40. The distance $D_2$ extending between the top surface 41 and the bottom surface 42 is any distance. In one embodiment, the distance between the top and bottom surfaces 41, 42 is no greater than 10 cm. In another embodiment, $D_2$ is 0.5 mm to 5 mm, most preferably about 4 mm.

In one embodiment, a rectangular base 40 has a first side 35 and a second side 36 separated by a distance $W_{12}$ and a first end 37 and a second end 38 separated by a distance $L_{10}$. In a more preferred embodiment, a base 40 is rectangular shaped with flattened corners. For example, a base 40 has a first side 35 and a second side 36 separated by a distance $W_{12}$; a first end 37 and a second end 38 separated by a distance $L_{10}$; and four corner ends, including a first corner end 45, a second corner end 46, a third corner end 47, and a fourth corner end 48.

Those of ordinary skill in the art will appreciate that the sides, ends, and corner ends of a base 40 are any length. In a preferred embodiment, the first and second sides 35, 36 are the same length; the first and second ends 37, 38 are the same length; and the four corner ends 45, 46, 47, 48 are the same length. In one embodiment, the length and width are the same. In another embodiment, the sides are longer in length than the ends. For example, the first side 35 and second side 36 each have a length $L_9$ of about 58 mm. The first end 37 and second end 38 each have a length $L_{11}$ that is about 12 mm. The four corner ends, including 45, 46, 47, and 48 each have a width $L_{13}$ that is about 2 mm.

A prong can be any shape and have any dimensions, including height. In this version of the invention, the general shape of the prong is a tapered rectangle. A prong comprises multiple edges, a prong top and a height. In one embodiment, a prong 43 has four edges, including an internal edge 49 and an external edge 52 which are opposed, and a first edge 50 and a second edge 51 which are opposed. In one embodiment, the surface of an inner edge 49 is flat and perpendicular to the top surface 41. The surface of the external edge 52 is flat and forms an angle $A_4$ with the top surface 41. In a preferred embodiment, the angle $A_4$ is 45 degrees. A first edge 50 has a surface that is concave and a second edge 51 has a surface that is concave. A prong top may be any shape and have any dimensions. In one embodiment, a prong top 55 is pointed. Alternatively, a prong top is rounded or flat. In one aspect of the invention, the prong top 55 is flat and rectangular shaped. In a further embodiment, the rectangular area of the prong top 55 is about 1 mm×2 mm. A prong (e.g., 44) may be any height. In a preferred embodiment, the height $H_6$ of a prong is about 5-6 mm.

In a preferred invention, a clamp 39 uses a set of at least two prongs to compress FOFs and a gasket together for the etching process. The surface of a base 40 has any number of prongs. Generally, prongs are aligned along the top surface 41. In one embodiment, a prong 43 is aligned on a top surface 41 with its external side 52 along a first side 35 and another prong 44 is opposed and aligned on a top surface 41 with its external side along a second side 36. A clamp 39 may have one or more pairs of prongs. In a preferred invention, a clamp 39 has multiple pairs of prongs. Preferably, a clamp 39 has one to six pairs of prongs aligned on its top surface 41. It is understood by one skilled in the art that the number of pairs of prongs can vary depending on the size of the FOF.

A pair of at least two prongs 43, 44 and base 40 form a unitary clamp 39 comprised from a single suitable material or from separate suitable materials which are integrally formed or mated together. In this version, the clamp 39 has a slot 56 located down the center of the top surface 41. The slot 56 is where the FOFs and gasket are held by the clamp 39. The slot 56 is created by the alignment of the prongs 43 and 44 on the top surface 41 along the first and second sides 35, 36. The length $L_{10}$ of slot 56 extends from the first end 37 to the second end 38. The width $W_{11}$ of slot 56 is the distance between the internal edges of a prong 44 and the internal edge of a prong 43. The slot can have any width and any length. The width $W_{11}$ of a slot 56 is generally equivalent to the width of two FOFs and a gasket sandwiched together. In a preferred embodiment, the width $W_{11}$ of the slot is about 6 mm. In a preferred embodiment, the length $L_{10}$ of the slot 56 is about 62 mm.

A clamp is comprised of any suitable material. In one embodiment, a clamp is fabricated from any acid resistant material. In a further embodiment, the clamp is fabricated from a plastic material. In a most preferred embodiment, the clamp is fabricated poly ether ether ketone ("PEEK clamp").

2. Gasket

The present invention includes a gasket as one of the pieces of hardware comprising an etch apparatus. The general purpose of a gasket is to form a seal between the gasket and one FOF surface in order to protect the other surface of the FOF from exposure to liquid (e.g., acid). A gasket is fabricated from a suitable material with properties compatible with the conditions of the chemical etching process. A gasket is generally comprised of an acid resistant material. In one embodiment, a material comprising a gasket is flexible. Those of ordinary skill in the art will appreciate that a gasket is any shape or size which is suitably shaped to form a seal with the FOF, such that the sealed area is correctly located on the FOF and protects the desired area from etching. A gasket has at least two surfaces e.g., a top and bottom surface. A gasket surface has a ridge, which is a flat, raised surface that makes contact with the FOF along the perimeter of the FOF around the area to be protected from the etching process. In one embodiment, a gasket has at least two opposed ridges which are flat raised surfaces that make contact with the FOF along the perimeter of the FOF around the area to be protected. In one embodiment, a gasket is rectangular in shape having two flat opposed surfaces with a distance in between the surfaces and each surface contains a ridge. The gasket has a protruding outer frame feature on both its top and bottom surface that serves to position the FOF in the proper location when it is mounted on the gasket. The outer frame of the gasket is comprised of walls which are permanently joined to the top and bottom surface. A gasket has any number of walls. In one embodiment, a gasket has four walls, including a first wall, a second wall, a third wall and a fourth wall. A gasket wall has a height. The gasket walls are connected at perpendicular angles to form a rectangular outer frame. The gasket walls, which comprise the outer frame of the FOF, extend above the top surface and below the bottom surface to form a tray-like structure into which each FOF is placed during the etch process. Preferably, a gasket is the same general shape as a FOF.

At least the top surface or the bottom surface or alternatively, both surfaces of a gasket include a raised portion which forms a ridge elevated above the surface, wherein the reason for such a ridge is to facilitate the formation of a tight seal between a FOF and the gasket surface and prevent one side of each FOF from exposure to liquid. The ridge is smooth and uniform in cross section and forms a continuous barrier around the perimeter of the FOFs. In one embodiment, a ridge is a rectangular shaped border which has a height above the gasket surface and a width. A ridge is located a distance inside the gasket walls.

A gasket further includes at least one index feature to provide a physical basis for properly orienting a FOF during the etch process, so that a FOF is only allowed to be mounted in a gasket in only one orientation. Proper positioning of a FOF ensures consistency that the same side of the FOF is etched. An index feature is any shape or form. In one embodiment, a band is positioned at an angle in one corner of a gasket to form a gasket index feature, wherein the band forms a corner barrier which restricts how a FOF is mounted into a gasket (i.e. the corner notch of a FOF must be matched to the gasket index feature).

Referring to FIGS. 11a-e, this version of the invention includes a gasket 75, including a top surface 76 and a bottom surface 77. The top and bottom surfaces 76, 77 are directly opposed, wherein there is a distance between the top surface 76 and the bottom surface 77. The distance between the two surfaces is any distance. In one embodiment, the distance $H_{10}$ between the top surface 76 and the bottom surface 77 is about 1 mm. A surface of a gasket can be any shape. In one embodiment, the top and bottom surfaces of a gasket are the same. In preferred embodiment, the top and bottom surfaces of a gasket are rectangular in shape.

It is understood by one skilled in the art that a gasket has any number of walls. In one embodiment, a gasket 75 has four walls, including a first wall 78, a second wall 79, a third wall 80, and a fourth wall 81. In a preferred embodiment, all of the walls of a gasket 75 are connected permanently. The walls are connected to form an outer frame permanently joined to opposed top and bottom surfaces 76, 77. In one embodiment, the walls 78, 79, 80, 81 of a gasket form a rectangular shaped frame around opposed top and bottom surfaces 76, 77. For example, in FIG. 11a, a first wall 78 and third wall 80 extend perpendicular between a second wall 79 and fourth wall 81.

The walls of a gasket 75 have a length which is any length. In one embodiment, the walls 78, 79, 80, 81 are the same length or alternatively different lengths. Suitable gaskets have walls that are different lengths. In a preferred embodiment, the length $L_4$ of first wall 78 is about 78 mm and the length of a third wall 80 is the same as length $L_4$ of the first wall 78. The width $L_6$ of a second wall 79 is about 42 mm and the length of a fourth wall 81 is the same as the length $L_6$ of a second wall 79.

In one embodiment, one or more walls of a gasket 75 extend to a height above the top surface 76. In a preferred embodiment, all of the walls 78, 79, 80, 81 extend to a height above and below the surfaces 76, 77. In a more preferred embodiment, a fourth wall 81 extends above the top surface 76 to a height $H_8$; a second wall 79 extends above the top surface 76 to a height $H_{12}$; a third wall 80 extends above the top surface 76 to a height $H_{14}$; and a first wall 78 extends above the top surface 76 to a height $H_{17}$. In a more preferred embodiment, the heights of each of the sides above the top surface $H_8$, $H_{12}$, $H_{14}$, and $H_{17}$ are the same. In a most preferred embodiment, the height $H_8$, $H_{12}$, $H_{14}$, and $H_{17}$ of each of the walls 81, 79, 80, 78 which extends above the top surface 76 is the same and about 2 mm.

In another embodiment, one or more walls of a gasket 75 have a height that extends below the bottom surface 77. In a preferred embodiment, a fourth wall 81 extends below the bottom surface 77 to a height $H_9$; a second wall 79 extends below the bottom surface 77 to a height $H_{13}$; a third wall 80 extends below the bottom surface 76 to a height $H_{15}$; and a first wall 78 extends below the bottom surface 77 to a height $H_{16}$. In a more preferred embodiment, the height $H_9$, $H_{13}$, $H_{15}$, and $H_{16}$ of each of the walls 81, 79, 80, 78 which extends below the bottom surface 77 is the same and about 2 mm.

Both surfaces 76 and 77 of a gasket contain a raised portion which is a ridge elevated above the surface. In one embodiment, both the top surface 76 and bottom surface 77 include a raised ridge. For example, a suitable ridge 85 is raised a height $H_7$ on a top surface 76 and a same ridge is found on a bottom surface 77. In one embodiment, the height $H_7$ of a ridge 85 is about 0.5 mm. A ridge 85 is continuous and the shape of a rectangle. A ridge 85 forms a border inside the walls of a gasket and is a distance $D_3$ from the walls of the gasket. In one embodiment, the distance $D_3$ of a ridge 85 from the wall of a gasket is about 1 mm. A ridge 85 has any width. In one embodiment, the width $W_{15}$ of a ridge is about 2 mm. In some suitable gaskets, there is at least one additional feature of the ridge which ensures that an effective seal is formed near the index feature between a FOF and the gasket. For example, a ridge 85 has an additional crossbar 84. Crossbar 84 has the same height and width as the rest of the ridge 85. A gasket has any number of cross bars.

In this invention, a gasket has at least one index features. An index feature of a gasket provides a physical basis for orienting a FOF so that the FOF mounts into a gasket in only one orientation. Consistent orientation of a FOF in a gasket ensures that the same single side of a FOF is protected from exposure to liquid. An index feature is located on the top surface 76 or the bottom surface 77 or alternatively, on both surfaces 76, 77 of a gasket. In one embodiment, a gasket includes at least one index feature which is a corner barrier 82, comprising a band 83 placed at an angle $A_5$ that provides a physical basis for orienting a FOF when the FOF is mounted into a gasket. In a preferred embodiment, the angle $A_5$ is 45 degrees. As a result of having a suitable index feature on a FOF (e.g., a corner notch) and a complementary index feature on a gasket (e.g., a corner barrier), proper mounting of a FOF 1 into a gasket occurs when the notched corner 13 of a FOF and a corner barrier 82 of a gasket are appropriately aligned. When a FOF and gasket are properly assembled, the polished surface 2 of a FOF 1 is consistently placed against a gasket 75 and therefore, the polished surface 2 is not exposed to acid and does not get etched.

A gasket is fabricated from a suitable material wherein the material is compatible with the conditions of the etch process. In one embodiment, a gasket is fabricated from an acid resistant material. Suitable materials for fabrication of a gasket are flexible. In one embodiment, the gasket is constructed of a flexible material. In a preferred embodiment, the gasket is comprised of silicone.

B. Chemical Etch Process

Figure 10:
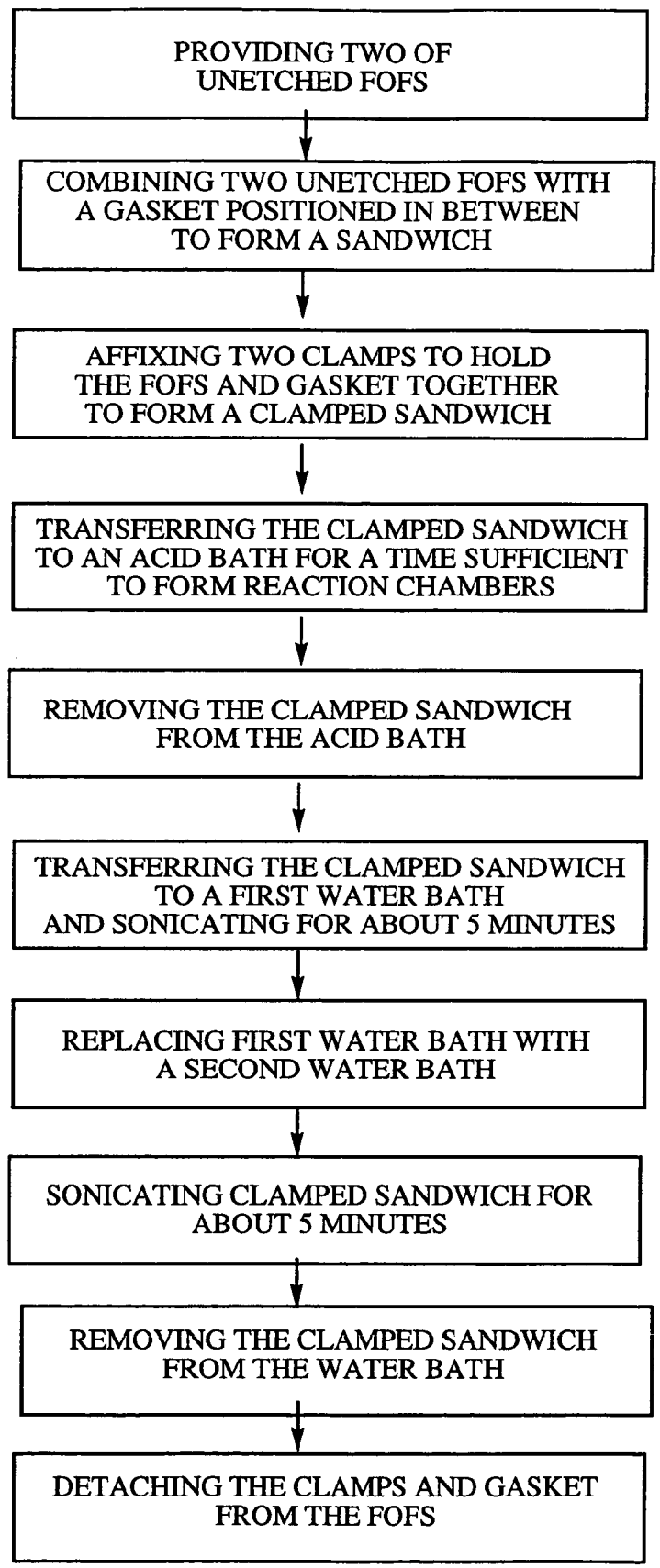
FIG. 10 is a process flow diagram illustrating the single-sided etching process.
Figure 11D:
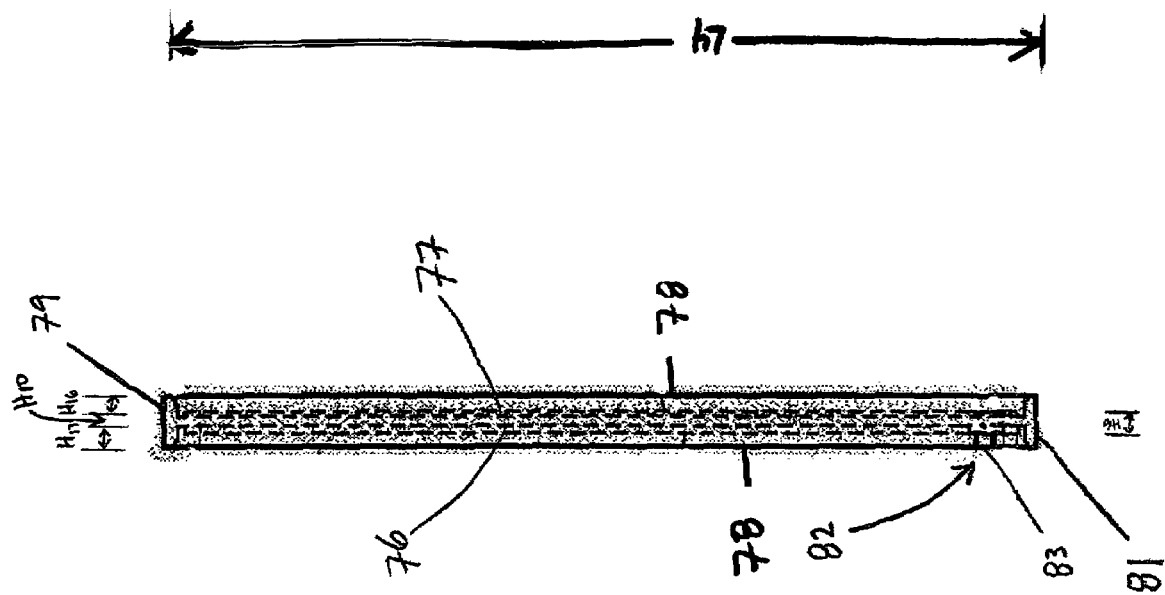
FIG. 11d is a drawing of an etch gasket (first side view)
Figure 11E:
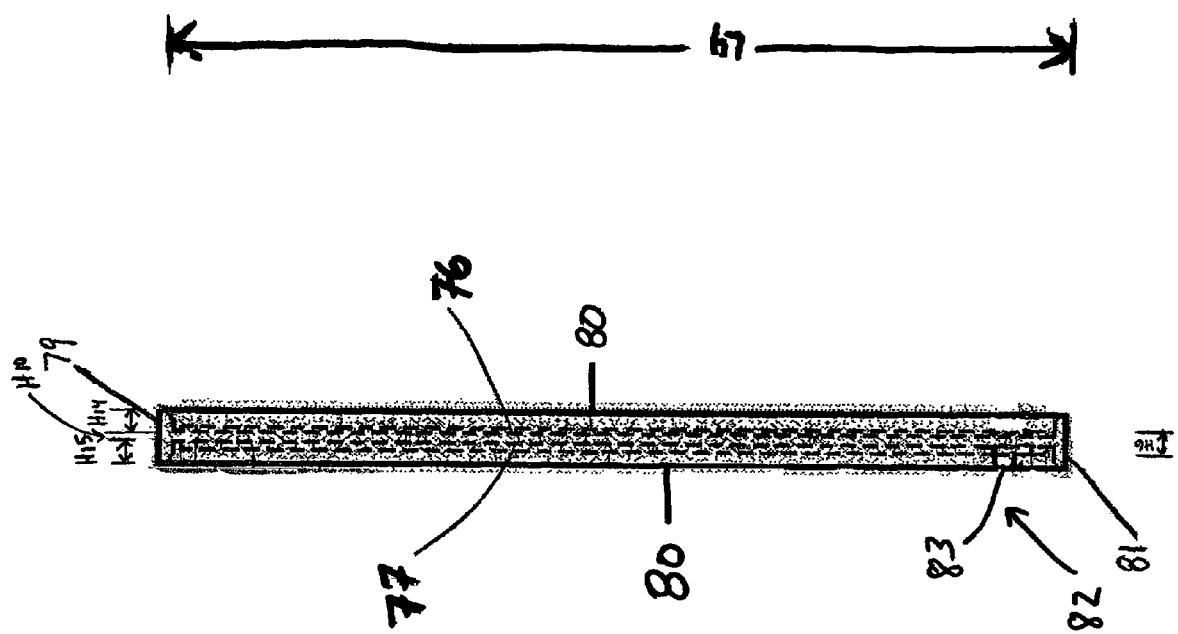
FIG. 11e is a drawing of an etch gasket (second side view)

The present invention provides a process that produces reaction chambers onto a single surface or side of a FOF. One suitable process is chemical etching, wherein the reaction chambers are etched onto a FOF using chemicals. In one embodiment, acid is the chemical used to etch the reaction chambers onto the FOF. In a further embodiment, a process for etching a single surface of a FOF requires that one surface of the FOF is protected such that the protected surface is not exposed to chemicals and therefore, does not get etched. A suitable process for etching a single surface of a FOF uses an apparatus (e.g., the apparatus described above, comprised of a set of clamps and a gasket) to protect one surface of a FOF from chemical exposure. In one embodiment, a FOF with reaction chambers etched onto one surface is produced using the process outlined in FIG. 10. Prior to chemical exposure, unetched FOFs are assembled using an etch apparatus comprised of a set of clamps and a gasket.

FIG. 13 shows an exploded view which illustrates the relationship of the various components utilized in the etching process, including a gasket 75 which is placed in between two unetched FOFs 1. A top surface 2 of a FOF 1 is mounted opposed to a top surface 76 of a gasket 75, wherein the corner notch 13 of the FOF 1 is matched with the complementary corner barrier 82 on the gasket 75. Two PEEK clamps 39 are affixed along the two longer, opposite sides of the sandwich 100 to firmly hold the FOFs 1 and gasket 75 together and to prevent the top surface 2 of the FOF from being exposed to acid. The entire assembly shown in FIG. 12 is referred to as a "clamped sandwich". The clamped sandwich 101 is transferred to an acid bath. In a preferred embodiment, the acid bath is comprised of 20% nitric acid (w/v aqueous solution). The time and conditions of the chemical etching reaction are adjusted to achieve control of the size and volume of the resultant reaction chambers. The clamped sandwich remains in the acid bath for a time sufficient to allow reaction chambers of the desired depth to form. In a preferred embodiment, the etch time is about 3 hours and 30 minutes, to produce reaction chambers with a reaction chamber depth of 55 µm. The process of fabricating reaction chambers can be adapted to any fiber size so as to provide a wide range of appropriately sized chambers. Generally, chambers are introduced into the termini of the fibers by placing the FOF into an acid bath for a variable amount of time. The amount of time is varied, depending upon the overall depth of the reaction chamber desired (see e.g., Walt, et al., 1996. *Anal. Chem.* 70: 1888).

3. Process for RER Cleaning

Figure 9:
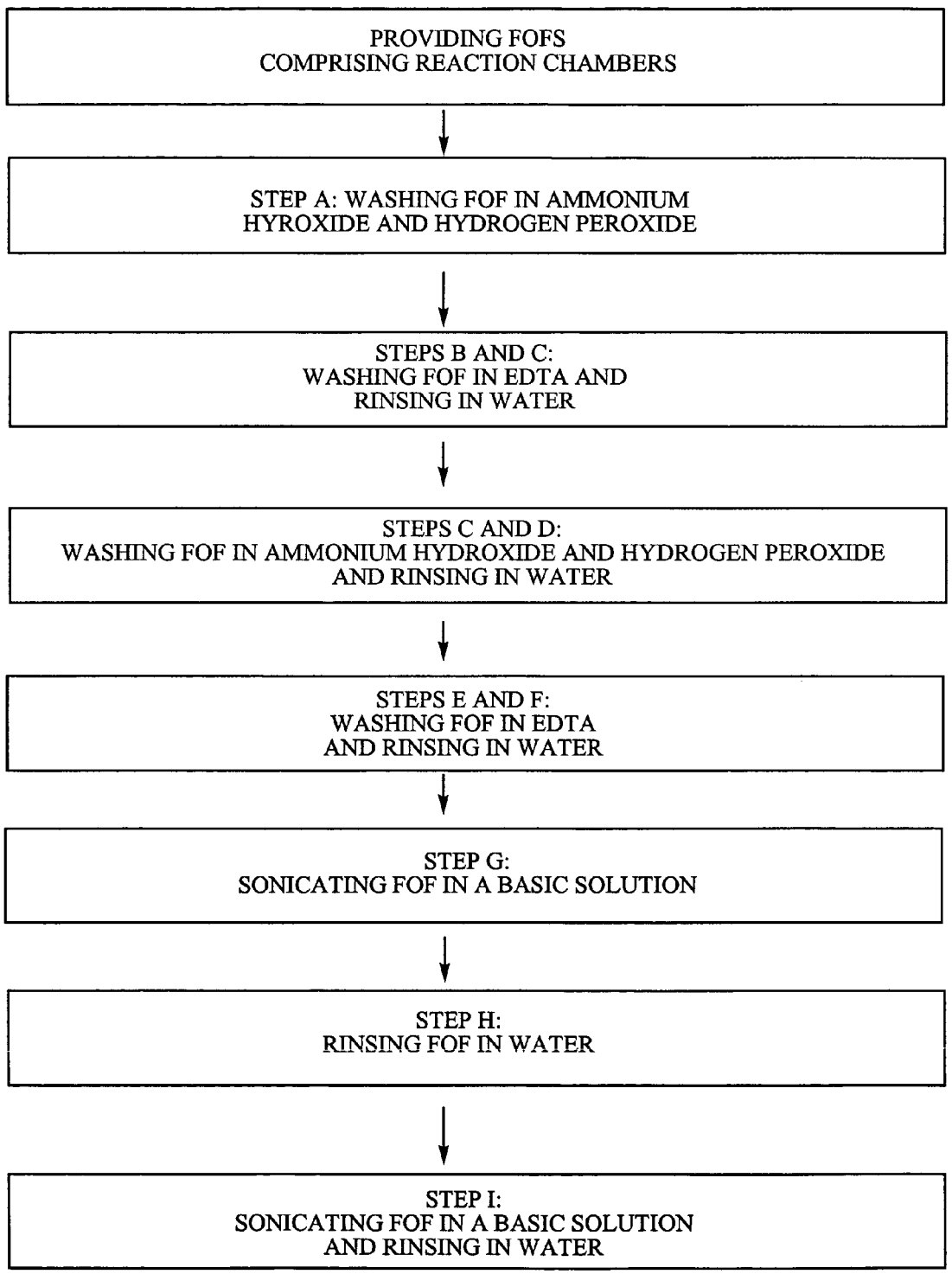
FIG. 9 is a process flow diagram illustrating the RER cleaning procedure.

Prior to thin film coating, all substrates (e.g., etched FOFs) are thoroughly washed to make the array surface free of gross particulate contaminants, and relatively free of oily contamination, such as fingerprints, prior to applying the thin film coating. In one embodiment, the FOF is thoroughly cleaned after the process etching of the reaction chambers is complete as described in Example 1 (FIG. 9). After cleaning, the FOF is coated with a thin film coating. Preferably the thin film coating consists of $SiO_2$ which is 0.1-5.0 microns thick, optically transparent, and impermeable to water.

4. Process for Coating Arrays

Several methods can be used for depositing a thin film onto the surface of an array substrate. These methods include vapor and liquid deposition processes. Both methods are described below.

A. Vapor Deposition

Vapor deposition is a method widely used in the semiconductor and optical components industry for which controlled processes are commercially available. In one embodiment, a thin film can be deposited from the vapor phase onto an array substrate. Vapor phase deposition processes are typically described as either physical or chemical in nature, depending on the extent to which the deposited film material is chemically transformed from its precursors. In one embodiment, a thin film is deposited on the substrate using a physical vapor deposition process known as sputtering or evaporation, whereby the chemical reagent which is the precursor to the thin film can be thermally evaporated in a vacuum chamber, with the "pre-film" vapor coating the array substrate and forming the thin film. See e.g., Plummer et al., Silicon VLSI Technology, Chapter 9, Prentice Hall, 2000. In one embodiment, a non-metal oxide is deposited as a thin film onto the array substrate using the sputtering or evaporation method of vapor deposition. In a preferred embodiment, the non-metal oxide $SiO_2$ is deposited using the sputtering or evaporation method (FIGS. 1a, 1b and 2b).

In another embodiment, a thin film can be deposited on the substrate using a chemical vapor deposition process known as plasma-enhanced chemical vapor deposition (PECVD), whereby two chemicals are reacted unto a heated substrate to produce a thin film. See e.g., Plummer et al., Silicon VLSI Technology, Chapter 9, Prentice Hall, 2000. In another embodiment, a non-metal oxide is deposited onto the array substrate using the PECVD method of vapor deposition. In a preferred embodiment, the non-metal oxide SiO2 is deposited onto the array substrate using the PECVD method (FIGS. 1c, 1d and 2c).

In one embodiment, the thin film can be deposited onto the array substrate using an ion-plating vapor deposition method which is a hybrid chemical-physical process. FIG. 3 shows a schematic of the ion-plating vapor deposition method. In a preferred embodiment, a non-metal oxide is deposited onto the array substrate using the ion-plating method of vapor deposition. In a preferred embodiment, the non-metal oxide, $SiO_2$ is the thin film deposited onto a FOF using the ion-plating method of vapor deposition (FIGS. 1e, 1f and 2d).

B. Liquid Deposition

Many liquid phase processes can be used to apply the thin film coating. Here, either the thin film or its precursor material are applied in liquid form to the array substrate, and the material subsequently solidifies. Liquid phase processes can be either physical or chemical or some combination. In one embodiment, the thin film material can be dissolved in a volatile solvent, the resulting solution is applied the array substrate and the solvent is allowed to evaporate, yielding a thin film of the coating material via a physical liquid phase process. In another embodiment, a thin film can be formed by a sol gel process, whereby inorganic silicates or organic siloxanes are dissolved in an appropriate solvent and applied to an array substrate. Upon drying and heating, the low molecular weight silicates/siloxanes undergo chemical condensation reactions to polymerize into a glass-like film via a hybrid physical-chemical liquid phase process.

Thin films deposited by liquid phase deposition can be applied to a substrate in a variety of ways. In one embodiment, substrates can be dipped into the coating solution and withdrawn in a controlled fashion, leaving a liquid coating with thickness controlled by the substrate withdraw rate and angle. In another embodiment, liquids can be applied by spin coating, where the thin film solution is applied to the substrate which is then spun to spread the liquid evenly over the surface and to remove any excess. In another embodiment, the thin film solution is sprayed on the substrate, where the coalescence of droplets produces a thin film. In another embodiment, a technique known as capillary coating can be used to coat an array. Capillary coating encompasses the use of a rolling cylinder partially immersed in the thin film solution. The substrate is moved close to the cylinder so that a meniscus is formed to the cylinder, and the cylinder is rotated at the same rate as the substrate is translated.

C. Quality Control

After the coating process is complete, the quality of the resulting thin film coating is evaluated using a number of different techniques. Both direct and functional methods are used to detect the presence of an intact thin film coating and to evaluate performance of the film-coated array. Initially, a visual quality control inspection is performed which consists of visually inspecting each film coated array for gross defects. Second, a single sample array is selected from each batch of arrays, and Scanning Electron Microscopy or "SEM" analysis is performed on the thin film coated array. Typically, SEM images of both the thin film coated surface and a prepared cross-section are collected and analyzed. Surface images are analyzed for defects and coating damage as well as for overall morphology of the thin film coated surface, while cross-sections are measured for thickness. Select arrays are also evaluated for any potential effects by components used in a chemical reaction or bioassay and contained in the reaction chamber (e.g., the thin film coating is examined both before and after "mock" PCR conditions, See, Example 3). The thickness of the thin film coating may be measured. In one embodiment, SEM is used to determine thickness of the thin film coating. In another embodiment, the thickness of the thin film coating can also be measured by adding a sapphire coupon (Corion Division, Franklin, Mass.) to the batch, and determining the thin film (e.g. $SiO_2$) thickness after the coating process is complete by measuring the wavelength dependence on its light transmittance.

The thin film coated arrays are also evaluated "functionally" regarding their performance for specific applications, e.g. DNA sequencing, to determine the effects of the thin film coating on PCR-induced sequencing background and overall quality of sequencing results. Such functional test can provide the advantage of single chamber resolution across the entire array surface. See, Example 4 and FIG. 4.

5. Methods of Using Arrays

Thin film coated arrays can contain a number of different reactants and analytes in their reaction chambers. In one embodiment, each reaction chamber of the thin film coated array contains reagents for analyzing a nucleic acid or protein. Typically those reaction chambers that contain a nucleic acid (not all reaction chambers in the array are required to) contain only a single species of nucleic acid (i.e., a single sequence that is of interest). There may be a single copy of this species of nucleic acid in any particular reaction chamber, or there may be multiple copies. It is generally preferred that a reaction chamber contain at least 100,000 copies of the nucleic acid template sequence, preferably at least 1,000,000 copies, and more preferably between 2,000,000 to 20,000,000 copies, and most preferably between 5,000,000 to 15,000,000 copies of the nucleic acid. For example, if the apparatus of the invention is to be used for a pyrosequencing reaction, the ordinarily skilled artisan will appreciate that changes in the number of copies of a nucleic acid species in any one reaction chamber will affect the number of photons generated in a pyrosequencing reaction, and can be routinely adjusted to provide more or less photon signal as is required. In one embodiment the nucleic acid species is amplified to provide the desired number of copies using PCR, RCA, ligase chain reaction, other isothermal amplification, or other conventional means of nucleic acid amplification. In one embodiment, the nucleic acid is single stranded.

The thin film coating provides an array with enhanced compatibility and functionality. One particular assay that has encountered problems due to array incompatibility is the analysis of nucleic acid molecules, specifically pyrophosphate sequencing (PPS) of PCR amplified nucleic acids. In one embodiment the thin film coated array is used to overcome a difficulty encountered in the PPS of PCR amplified nucleic acids. The PPS method used is according to the methods of U.S. patent application Ser. No. 10/767,779. See also, U.S. Pat. No. 4,863,849 and U.S. Pat. No. 4,971,903. When amplification is performed, followed by sequencing in the same reaction chamber, a "background" signal is observed. The source of this background is the released pyrophosphate (PPi) which remains strongly bound to the reaction chamber of the FOF such that it persists even after extensive washing. Therefore, a "background" assay was developed which involves performing solution phase PCR, washing the FOF, loading the FOF with Dynal sulforylase (S) and luciferase (L) beads (Fisher Scientific, Pittsburgh, Pa.), and measuring the signal (normalized to an earlier pyrophosphate flow). A reduction in the background noise in PPS would result in better sequencing results at a given signal level or allow equivalent sequencing result to be obtained at lower signal levels (Example 5).

Figure 4:
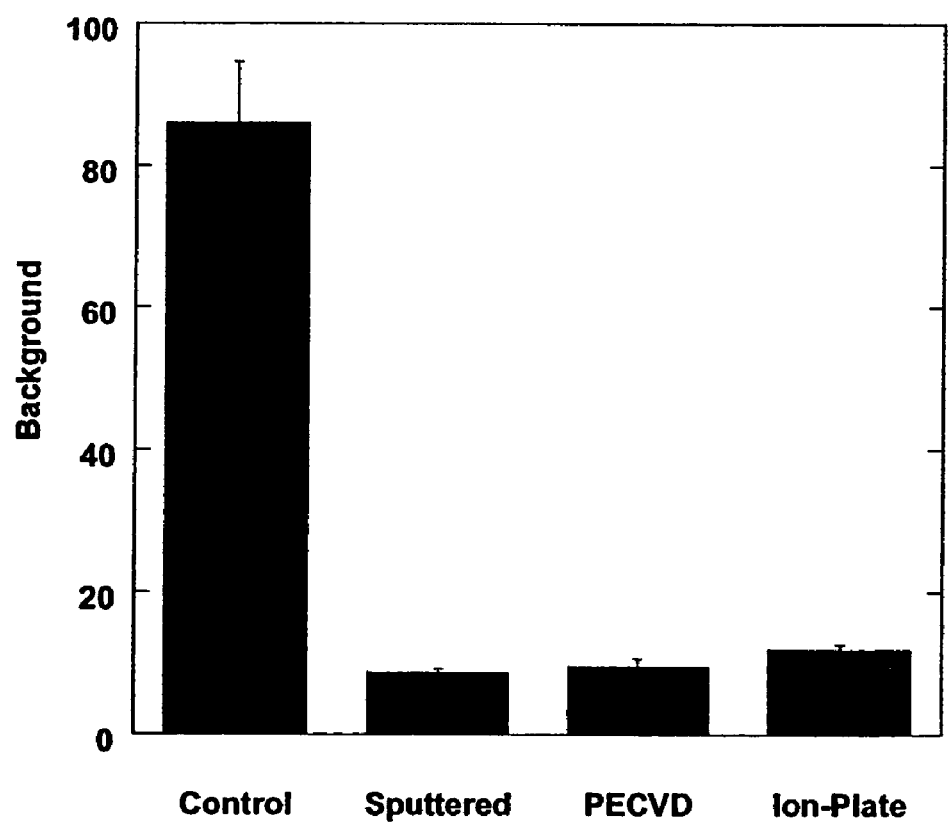
FIG. 4 is a bar graph showing PCR-induced sequencing backgrounds of $SiO_2$ coated and uncoated fiber optic faceplates comprising reaction chambers.
Figure 5:
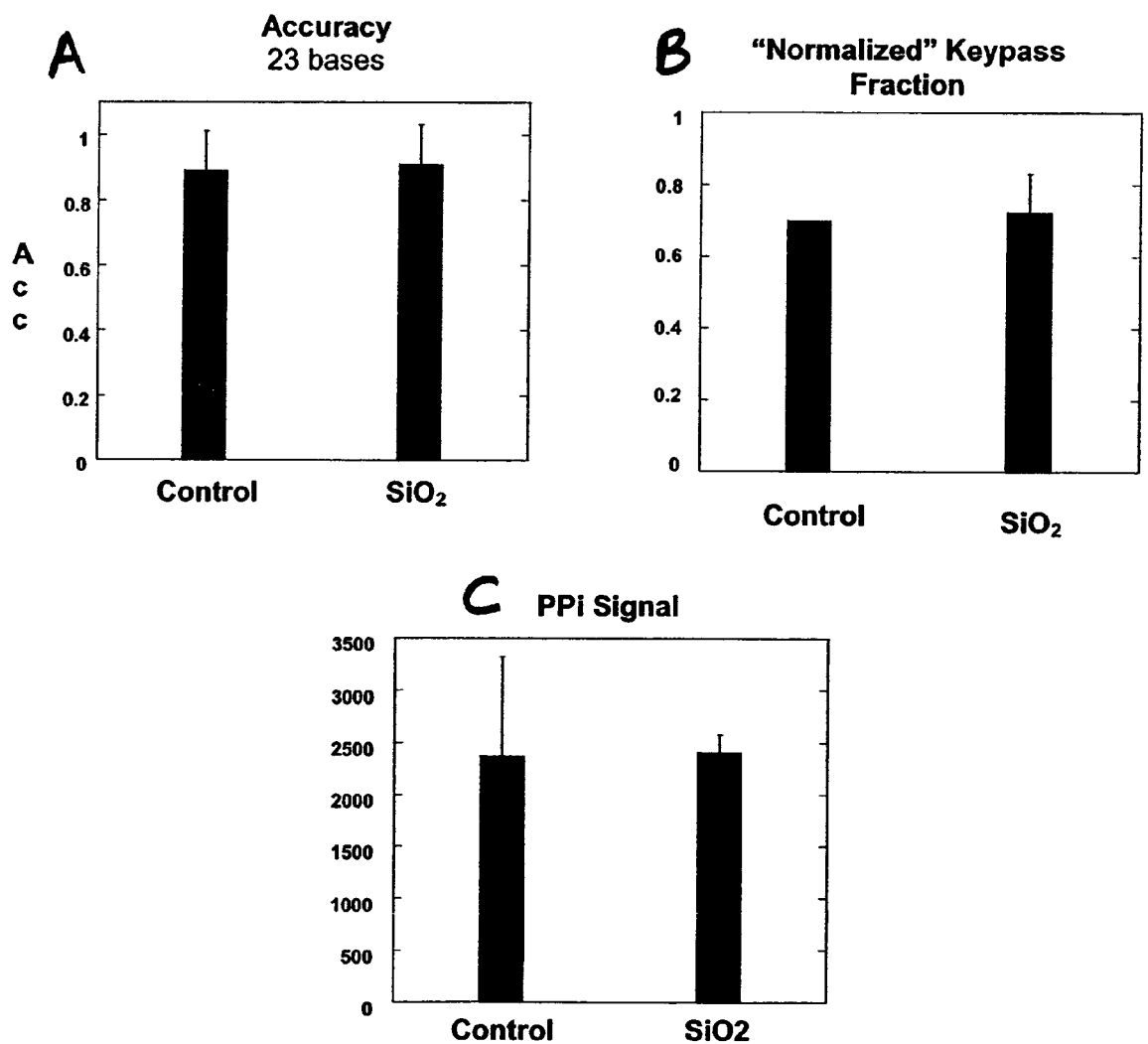
FIG. 5 is a series of graphs showing sequencing performance metrics of $SiO_2$ coated and uncoated fiber optic faceplates comprising reaction chambers for accuracy (FIG. 5a), "normalized" keypass fraction (FIG. 5b), and pyrophosphate (PPi) signal (FIG. 5c)
Figure 7A:
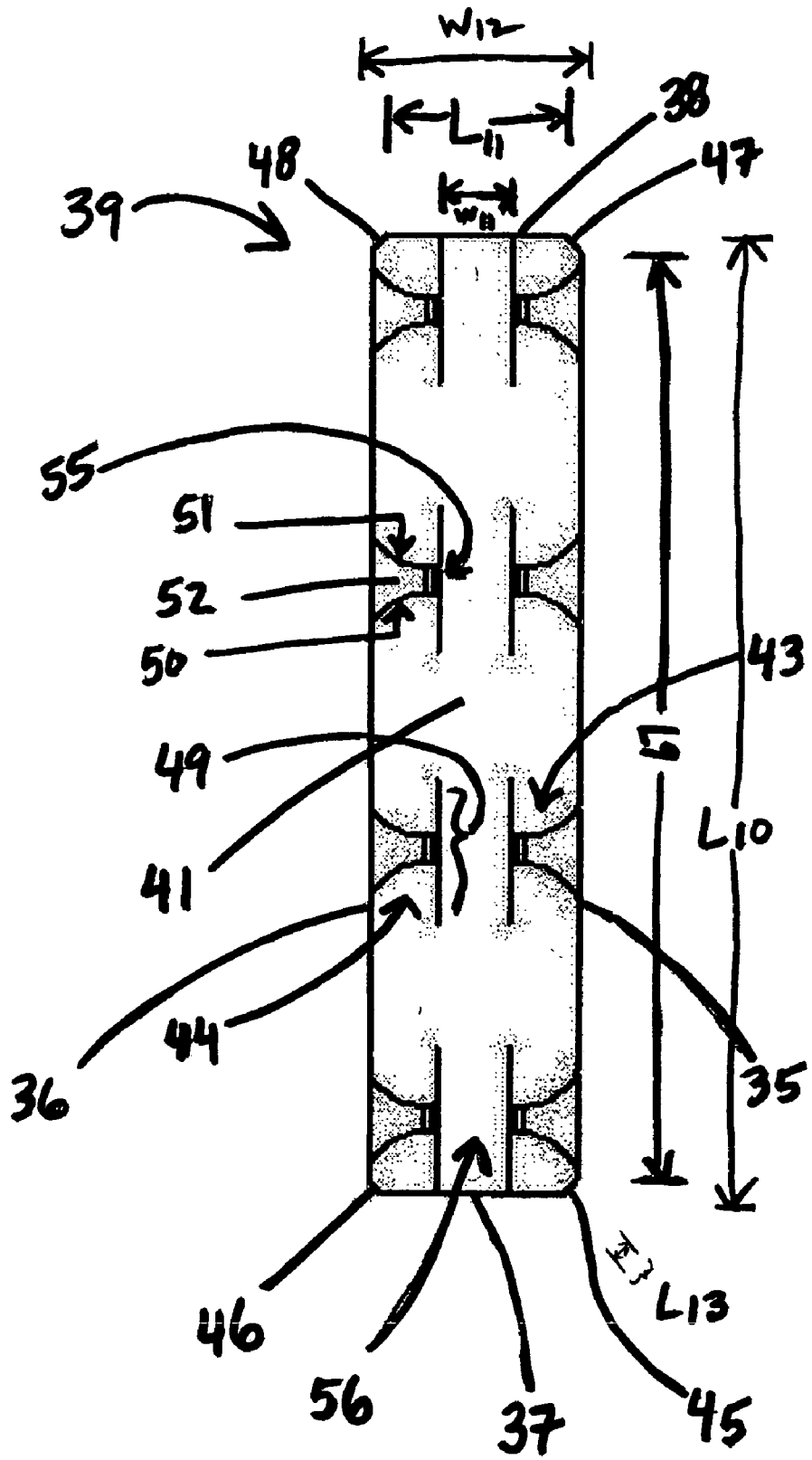
FIG. 7a is a drawing of a PEEK clamp (top view)

Thin film coatings on the reaction chamber of a microwell array can significantly reduce PCR-induced sequencing background as shown in FIG. 4. In a preferred embodiment, a thin film coating of $SiO_2$ with a thickness of 01.-5.0 microns on a FOF significantly reduces the PCR-induced sequencing background and provides for the same sequencing results as obtained in an uncoated array as shown in FIG. 5.

EXAMPLES

The following examples have been selected merely to further illustrate features, advantages, and other details of the invention. It is to be expressly understood, however, that while the examples serve this purpose, the particular conditions and details are not to be construed in a manner that would unduly limit the scope of this invention.

Example 1

General Etching Process and RER Cleaning Procedure

This example describes the general single-sided etching process for FOFs (Incom Corporation, Charlton, Mass.) sizes 25×75 mm or 40×75 using silicon etch gaskets and PEEK (Poly Ether Ether Ketone) plastic clamps (FIGS. 11a and 11b). Distilled water for the Branson Ultrasonic bath (Fischer Scientific, Hampton, N.H.), preferably from a PicoPure™ water purification unit ("PicoPure water"), was degassed for 10 minutes. The NesLab recirculator (Portsmouth, N.H.) was set to 57.2° C. (at this setting, water inside the ultrasonic bath was maintained at a constant temperature of 55° C.). Four stainless steel containers were covered and placed in the ultrasonic bath. Each container was charged with 1000 mL (for a 25×75 mm FOF) and 1200 mL (for a 40×75 mm FOF) of 20% $HNO_3$ and warmed to 55° C. Ninety-six unetched FOFs were loaded into each of the 96 positions of four etch trays. A designated FOF was selected and weighed. The difference in FOF weight before and after etching was plotted in order to correlate weight loss to reaction chamber depth.

A pair of unetched FOFs was combined by positioning a silicon gasket (FIG. 13) in between the two FOFs and properly aligning each, such that the polished side of each FOF is facing the gasket and within the edge of the gasket. The corner notch of the FOF is aligned with the corner barrier on the gasket. The first PEEK clamp was affixed to hold the two FOFs and gasket together vertically and squeeze the plates together. The clamp was snapped on down the center of the long end of the FOFs starting with the bottom-most clip. The second PEEK clamp was applied. The finished clamped sandwich is shown in FIG. 12. The remaining unetched FOFs were combined and clamped as described above. Next, 12 sandwiches were positioned into each of the four stainless steel racks. Once the temperature of the $HNO_3$ reached 55° C., the ultrasonic bath was turned on and the lids of the other 3 stainless steel containers removed. Each of the four stainless steel racks holding FOFs was transferred into the acid at 55° C. The FOFs were kept in the 55° C. acid bath. The etch rate of the FOFs was approximately 0.245 μm/min. The length of time that the FOFs remained in the bath depends on the desired reaction chamber depth. For example, an etch time of 3 hours and 44 minutes resulted in a reaction chamber depth of 55 μm.

The etched FOFs (i.e. FOFs) were removed from the acid bath and placed directly into stainless steel containers filled with 1.0 L of PicoPure water, and sonicated for 5 minutes. The water was discarded and the containers were filled with 1.0 L of PicoPure water, and sonicated for an additional 5 minutes. The FOFs were removed from the rinse water and PEEK clamps and silicon gaskets were detached from each pair of FOFs.

To complete the post etch testing, the designated FOF was re-weighed and change in weight due to the etching was recorded. A count of the number of individual fibers with impaired optical transmission (a "dark fiber count") was preformed using a microscope.

A five step RER cleaning procedure using RCA cleaner, and ethylenediamine tetra-acetic acid (EDTA) ("RER cleaning procedure") for etched FOFs was conducted. "RCA" is the abbreviation for a solution of ammonium hydroxide ($NH_4OH$) and hydrogen peroxide ($H_2O_2$). To prepare RCA cleaner 1.0 L of $NH_4OH$ and 1.0 L of $H_2O_2$ were combined under a hood and the solution was mixed using a magnetic stir bar. Ninety-six (96) FOFs from the same lot were placed into the glass slide racks.

Step 1—First RCA Wash

RCA cleaner was prepared by combining a 1:1 solution of $NH_4OH$ and $H_2O_2$. For the 25×75 mm FOF, 200 mL of RCA cleaner was added to each of the glass staining dishes (Fisher Scientific, Pittsburgh, Pa.). For the 40×75 mm FOF, 200 mL of RCA cleaner was added to the polypropylene staining dishes. Six staining dishes were placed into the container of one rotator of an Ocelot Rotator (Boekel Scientific, Feasterville, Pa.) and the other dishes were placed on the other rotator. The shake speed was set at C. After 30 minutes, the RCA cleaner was disposed. Each set of 10 FOFs was rinsed 5 times with 200 mL of PicoPure water.

Step 2—First EDTA Wash

EDTA (200 mL) was added to each staining dish. The six dishes were placed into the container on one of the rotators and the other 4 dishes were placed into the container on the other rotator. The shake speed was set at C. After 30 minutes, the EDTA was disposed. Each set of 10 FOFs was rinsed with 200 mL of PicoPure water 5 times.

Step 3—Second RCA Wash

A fresh solution of RCA cleaner (1:1 $NH_4OH$ and $H_2O_2$) was prepared and 200 mL of RCA cleaner was added to each of the staining dishes. The six dishes were placed into the container on one of the rotators and the other 4 dishes were placed into the container on the other rotator. The shake speed was set at C. After 30 minutes, the RCA cleaner was disposed. Each set of 10 FOFs was rinsed with 200 mL of PicoPure water 5 times.

Step 4—Second EDTA Wash

EDTA (200 mL) was added to each staining dish. The six dishes were placed into the container on one of the rotators and the other 4 dishes were placed into the container on the other rotator. The shake speed was set at C. After 30 minutes, the EDTA was disposed. Each set of 10 FOFs was rinsed with 200 mL of PicoPure water 5 times.

Step 5—Sonicating the FOFs

The NesLab recirculator was charged with the appropriate amount of water and the temperature point was set to 40° C. with the low temperature alarm at 5° C. and the high temperature alarm at 100° C. The FOFs were placed into a stainless steel rack (Fisher Scientific, Pittsburgh, Pa.) loading the FOFs into every other slot to allow for good flow of the cleaning solution. The filled racks were placed into a polypropylene pan filled with a 5% Contrad® solution with the solution completely covering the FOFs. The 5% Contrad® solution was prepared by combining 1000 mL of deionized water with 50 mL of Contrad® (Fisher Scientific). The pans were then covered with a HDPE (high density polyethylene) cover. When the temperature of the recirculator reached 40° C., two polypropylene pans containing the FOFs were submerged in the water. The FOFs were sonicated for 90 minutes and then removed from the sonicator. The racks were removed from the pans and the Contrad® solution drained. The polypropylene pans were filled with PicoPure water. The stainless steel racks were placed back in the pan and the FOFs were rinsed 2 times. The pan was refilled a third time with PicoPure water and taken to the Ocelot Rotator and rotated on speed C. After 5 minutes, the FOFs were rinsed with water 2 times. The FOFs were covered with tin foil and allowed to dry in the stainless steel racks.

Example 2

FOF Coating Using Ion-Plating Deposition Method

FOFs were immediately cleaned prior to thin film coating. The detergent used was Contrad®. The Branson sonicator was set to 40° C. Two FOFs were placed back to back in a Falcon tube, and 40-45 mL of 5% Contrad® solution was added in the tube and the cap closed. The tube was loaded in the sonicator and sonicated for 90 min. FOFs were removed from the tube, rinsed thoroughly with fresh deionized water, and transferred to a new Falcon tube and filled with deionized water. The detergent solution was disposed in the sink and FOFs kept in de-ionized water at 4° C.

After cleaning, the ion-plating process for coating a chemically etched FOF with a thin film $SiO_2$ coating was performed. The FOF to be coated was placed on an electrically isolated holder in a vacuum chamber, along with an electrically isolated heated silicon target, an argon plasma source, and a source of oxygen. The argon plasma source was ignited, which generated an overall negative charge on the FOF. Silicon vapor was produced by evaporation of the heated target, and reacted with the argon plasma, as well as the oxygen to form positively charged $SiO_2$ species. These $SiO_2$ species attract to the negatively charged FOF, where they energetically condense, forming a glassy, unstructured $SiO_2$ film. The film morphology and homogeneity is a complex function of many process variables, but the film thickness was precisely controlled by the exposure time in the chamber. See FIGS. 1 and 2.

Example 3

Exposure of the Thin Film Coated FOF to "Mock" PCR Conditions

Thin film coated, etched FOFs were tested for environmental robustness by exposing the thin film, coated etched FOF to deionized water at temperatures (approximating PCR thermal exposure), and examining SEMs of both the surfaces and cross-sections for signs of coating damage according to the following procedure. One milliliter of 1×HiFi PCR buffer (Invitrogen, Carlsbad. Calif.) was prepared. The thin film, etched FOF was placed on top of tissues and using a cell scraper, the excess water was removed. Quickly, 400 μL of the buffer was added on top of the FOF surface and the solution was evenly spread out with a cell scraper. After 1 minute, the excess solution was removed. The procedure of adding 400 μL of the buffer followed by removing the solution was repeated. The FOF was immediately placed in an in-house amplification device (the "AMP jig") (454 Life Sciences, Branford, Conn.), covered with a silicon rubber plate and foam, and the AMP jig screws were tightened as described in Leamon et al., Electrophoresis 24: 3769-3777 (2003). The AMP jig was loaded into a Thermocycler MJ PTC 225 Tetrad (MJ Research, Waltham, Mass.) and the thermocycling program was run. The details of the temperature profile were as follows: total run time is 4.5 hours, 1) 40 short cycles: 94° C.: 15 sec; 58° C.: 15 sec; 68° C.: 15 sec; 2) 10 additional long cycles: 95° C.: 30 sec; 58° C.: 10 min. The procedure was repeated for a total of 80 cycles. After thermocycling, the FOF surface was rinsed with fresh water. The surface was dried with nitrogen flow and the $SiO_2$ coating was measured by optical microscopy and SEM. Since SEM is a destructive technique, "before" and "after" analysis of the same thin film etched FOF could not be performed. However, all thin film etched FOFs examined by SEM after the above "mock-PCR" procedure showed no apparent damage to the thin film coatings.

Example 4

Evaluation of PCR-Induced Sequencing Background

A 1 mL LuerLock® syringe (20G1) (Becton Dickinson, Franklin Lakes, N.J.) was charged with 525 μL of PCR solution (1× Platinum HiFi Buffer (Invitrogen, Carlsbad, Calif.), 2.5 mM MgSO4, 0.5% BSA, 1 mM dNTPs (MBI Fermentas, Hanover, Md.) and the syringe needle was connected to an in-house loading device (the "loading jig") (454 Life Sciences, Branford, Conn.). dNTP refers to the 4 deoxynucleotide triphosphates (dATP, dCTP, dGTP, and dTTP). A thin film coated, etched FOF was removed from a deionized water bath, placed on the lab bench and using a cell scraper, excess water was removed from the FOF surface. The FOF was quickly assembled on the loading jig with 4 plastic clips. The fluid chamber was filled to the top with PCR solution by pushing the syringe forward. After 3 minutes, the solution had diffused into the reaction chambers. The plunger was pulled back and the loading jig disassembled. The FOF was immediately placed in an AMP jig and covered with a silicon rubber plate and foam. Jig screws were put in place and tightened. The jig assembly was loaded in the Thermocycler and the thermocycling program was run. The details of the temperature profile were as follows: total run time is 4.5 hours, 1) 40 short cycles: 94° C.: 15 sec; 58° C.: 15 sec; 68° C.: 15 sec; 2) 10 additional long cycles: 95° C.: 30 sec; 58° C.: 10 min.

After thermocycling, the AMP jig was opened, the FOF was removed and placed in a 50 mL Falcon tube (Becton Dickinson, Franklin Lakes, N.J.) containing 50 mL of deionized water. The tube was then positioned on a Clay Adams® Nutator Mixer and nutated for 20 min to dissolve the PCR product. Nutation is a gentle orbital motion that can assure uniform mixing without foaming. The FOF was transferred into 50 mL of Assay Buffer ("AB") with BSA (bovine serum albumin). AB is a buffer solution containing tricine and magnesium acetate. The resulting solution was collected for the PCR sequencing analysis described in the following example (Example 5).

The bead mixture was prepared (Bangs beads 175 μL+Dynal beads 175 μL) and diluted with 700 μL of deionized water. Bangs beads are microspheres carrying immobilized sulfurylase and luciferase enzymes, and dynal beads are magnetic beads carrying the bound enzymes of luciferase and sulfurylase. Nineteen adhesive pads (3M VHS, St. Paul, Minn.) containing 13.2 μL of bead mixture each were used to seal the inlet holes. The FOF was then spun using an Allegra 6R Centrifuge (Beckman Coulter, Fullerton, Calif.) for 8 minutes at 2000 rpm. The background run was performed and total time was 24 min: 1) wash 5 min; 2) PPi 2 min; 3) wash 10 min; 4) PPi 2 min; and 5) wash 5 min). After the run, a trace analysis was performed using Kangaroo software (454 Life Sciences, Branford, Conn.). Adjusted counts were obtained by subtracting 500 from raw counts. The whole procedure was repeated for both uncoated and coated FOFs for background comparison.

Example 5

PCR Sequencing Results

For validation of PCR results, uncoated and $SiO_2$ coated FOFs were paired and tested simultaneously using the solution collected for analysis in Example 5. Each solution (for both SiO2 coated and uncoated arrays) was doubled by dilution with deionized water. Then, the PCR product in each was quantitated using an iCycler® RealTime PCR unit (Bio-Rad, Hercules, Calif.). Using fluorescence measurements, the amount of amplified product was determined. Finally, the number of molecules per reaction chamber after PCR was calculated. Normal range of the number is $10^3$-$10^9$ order. The results are shown in Table 2 below and the results are in the range of $10^6$-$10^8$ and are acceptable. All of the $SiO_2$ coated FOFs produced equal level of the PCR product compared to the uncoated FOFs.

TABLE 2

Results of in-reaction chamber PCR

| FOF Number | Molecules/Reaction Chamber |
|---|---|
| Uncoated (Control) | |
| FOF #1 | $8.21 \times 10^7$ |
| FOF #2 | $1.10 \times 10^8$ |
| $SiO_2$-coated | |
| FOF #3 | $1.70 \times 10^8$ |
| FOF #4 | $3.98 \times 10^7$ |
| FOF #5 | $1.70 \times 10^8$ |
| FOF #6 | $4.40 \times 10^7$ |
| FOF #7 | $8.16 \times 10^7$ |
| FOF #8 | $6.04 \times 10^6$ |

Example 6

$SiO_2$ Thin Film Coated Microwell Array

In a particularly preferred embodiment, the array apparatus for nucleic acid sequencing is formed from a commercial FOF (Incom, Charlton, Mass.) which has been chemically etched on a single side with acid to yield individual reaction chambers. The apparatus used to etch an FOF comprises two PEEK clamps and a silicone etch gasket. Each reaction chamber formed by etching has a volume of most preferably about 75 pL. The FOF is cleaned prior to coating with a thin film. The preferred thin film coating is the non-metal oxide $SiO_2$ with a thickness measuring 0.1-5.0 microns thick. The $SiO_2$ coating is optically transparent and impermeable to water. The thin film coating is applied using an ion-plating vapor deposition method. The use of film coated reaction chambers on a FOF surface serves several purposes; i) delayed diffusion of the luminescence from emitting light in a different region of the array, ii) isolation of reaction chambers that contain components of the assay solution or reaction mixture protected from any deleterious effects of the array substrate material, and iii) prevention of any leaching of substrate materials into the chamber solution, and iv) very efficient, high numerical aperture optical coupling to the CCD. Finally, the larger the amount of reactant (e.g. immobilized sequencing template) or analyte within a reaction mixture or assay solution, the more optical signal one is able to achieve.

What is claimed:

1. An array comprising:
   a fiber optic faceplate substrate that comprises:
   a planar top surface comprising a plurality of reaction chambers and an optically transparent silicon dioxide thin film coating disposed on the surface of said reaction chambers that is from 0.1-5.0 microns thick and is impermeable to water;
   a polished optically conductive planar bottom surface;
   a first and a second side edge each comprising a bevel of about 45 degrees located along the optically conductive planar bottom surface and
   a notch removed from a corner of the fiber optic faceplate that connects the first side and a first end at an angle of about 45 degrees;
   wherein the first and the second beveled side edges and the notch operatively couple to a retaining structure within an analytical instrument and provide proper positioning of the reaction chambers and the optically conductive planar bottom surface relative to a fluidic chamber and an imaging system within the analytical instrument.

2. The array of claim 1, wherein the spacing between the center points of two adjoining reaction chambers is between 5 μm to 200 μm, and each reaction chamber has a width in at least one dimension of between 4 μm and 190 μm.

3. The array of claim 1, wherein the number of reaction chambers is less than 10,000.

4. The array of claim 1, wherein the number of reaction chambers is greater than 10,000.

5. The array of claim 1, wherein the depth of substantially all of the reaction chambers is between 10-100 μm.

6. The array of claim 1, wherein the depth of substantially all of the reaction chamber is 50-55 μm.

7. The array of claim 1, wherein the polished optically conductive planar bottom surface is optically transmissive such that optical signals from the reaction chambers are detected by the imaging system through the polished optically conductive planar bottom surface, wherein the distance between the top surface comprising the reaction chambers and the polished optically conductive planar bottom surface is no greater than 5 mm in thickness.

8. The array of claim 1, wherein the thin film coating is 200-400 nm thick on the surface of the reaction chambers.

9. The array of claim 1, wherein the thin film coating is 50-100 nm thick on the side walls of the reaction chambers and 100-300 nm thick on the bottom of the reaction chambers.

10. The array of claim 1, wherein the fiber optic faceplate substrate is marked with one or more identifier codes.

11. The array of claim 10, wherein the one or more identifier codes are selected from the group consisting of a barcode, a data matrix code, and an alpha-numeric code.

12. The array of claim 10, wherein the analytical instrument does not operate unless at least one of the identifier codes is readable by the analytical instrument.

13. The array of claim 12, wherein the analytical instrument reads the identifier codes using a CCD camera or a bar-code reader.

14. The array of claim 10, wherein the identifier codes are marked by etching or printing.

15. The array of claim 10, wherein at least one of the identifier codes provides a visual orientation reference of the fiber optic faceplate substrate when operatively coupled to the retaining structure in the analytical system.

16. The array of claim 1 further comprising:
   a data collection system in communication with the imaging system.

* * * * *